(12) United States Patent
Chung et al.

(10) Patent No.: US 7,037,491 B2
(45) Date of Patent: May 2, 2006

(54) HUMAN THROMBOPOIETIN COMPRISING GLYCOSYLATION SITED AT RESIDUES 157 AND 164

(75) Inventors: Joo Young Chung, Sungnam-si (KR); Sang Kyu Park, Seoul (KR); Sang Myoung Ju, Sungnam-si (KR); Hyea Kyung Ahn, Sungnam-si (KR); Seung Wook Lim, Sungnam-si (KR); Woo Ik Chang, Koonpo-si (KR); Seung Kook Park, Sungnam-si (KR); Yeo Wook Koh, Sungnam-si (KR); Ji Soo Park, Seoul (KR)

(73) Assignee: Daewoong Pharmaceutical Co., Ltd., Seoul (KR)

( * ) Notice: Subject to any disclaimer, the term of this patent is extended or adjusted under 35 U.S.C. 154(b) by 13 days.

(21) Appl. No.: 11/043,387

(22) Filed: Jan. 26, 2005

(65) Prior Publication Data

US 2005/0186603 A1 Aug. 25, 2005

Related U.S. Application Data

(62) Division of application No. 10/441,729, filed on May 20, 2003, which is a division of application No. 09/720,410, filed on Dec. 21, 2000, now abandoned.

(30) Foreign Application Priority Data

Jun. 29, 1999 (KR) ................................. 1999-25143
Jun. 30, 1919 (KR) ................................. 1998-25935

(51) Int. Cl.
*C07K 14/52* (2006.01)
(52) U.S. Cl. ................... 424/85.1; 530/395; 530/351; 435/69.5; 435/358; 435/320.1
(58) Field of Classification Search .................. None
See application file for complete search history.

(56) References Cited

U.S. PATENT DOCUMENTS 5,756,083 A 5/1998 Elliott 6,451,554 B1 9/2002 Wood et al.

FOREIGN PATENT DOCUMENTS

| EP | 0 668 352 A1 | 8/1995 |
|---|---|---|
| WO | WO 95/18858 | 7/1995 |
| WO | WO 95/21920 | 8/1995 |
| WO | WO 95/26746 | 10/1995 |
| WO | WO 96/17062 | 6/1996 |
| WO | WO 96/23888 | 8/1996 |
| WO | WO 96/25498 | 8/1996 |

OTHER PUBLICATIONS

K. H. Pearce, Jr., et al., "Mutational analysis of thrombopoietin for identification of receptor and neutralizing antibody sites", Journal of Biological Chemistry 272(2): 20595-20602, Aug. 15, 1997.

Hoffman et al., "Peptide, Disulfide, and Glycosylation Mapping of Recombinant Human Thrombopietin Ser 1 to Arg 246", *Biochemistry*, 1996, 35(47), 14849-14861 (Eng.) Columbus, OH, USA: Chemical Abstracts, vol. 126, No. 6, Feb. 10, 1997, p. 80, Abstract No. 70279s.

Park et al., "Identification of Funtionally Important Residues of Human Thrombopoietin", *The Journal of Biological Chemistry*, vol. 273, No. 1, Jan. 2, 1998, pp. 256-261.

Sareneva et al., "Role of N-glycosylation in the Synthesis, Dimerization and Secretion of Human Interferon-γ", *Biochem. J.*, (1994) 303, pp. 831-840.

Asano et al., "The role of N-glycosylation in the targeting and stability of GLUTI glucose transporter", FEBS 12589, vol. 324, No. 3, Jun. 1993, pp. 258-261.

*Primary Examiner*—Lorraine Spector
(74) *Attorney, Agent, or Firm*—Gates & Cooper LLP

(57) ABSTRACT

The present invention relates to novel human thrombopoietin (hTPO) derivatives, and to process of preparation thereof. Particularly, sugar chains are introduced into native hTPO by substituting amino acids such as asparagine for amino acids at specific positions in native hTPO, preparing novel hTPO derivatives with high activities enhancing the platelet production in vivo. Therefore, the novel hTPO derivatives of this invention may be useful for the treatment of thrombocytopenia associated with anticancer therapy or the transplantation of bone marrow.

7 Claims, 12 Drawing Sheets

SEQUENCE LISTING

<160> NUMBER OF SEQ ID NOS: 34

<210> SEQ ID NO 1
<211> LENGTH: 23
<212> TYPE: DNA
<213> ORGANISM: Artificial Sequence
<220> FEATURE:
<223> OTHER INFORMATION: BglII-tagged primer corresponding to the N
      terminal sequence of hTPO protein

<400> SEQUENCE: 1
gaagatctat ggagctgact gaa                                              23

<210> SEQ ID NO 2
<211> LENGTH: 24
<212> TYPE: DNA
<213> ORGANISM: Artificial Sequence
<220> FEATURE:
<223> OTHER INFORMATION: EcoRI-tagged primer corresponding to the C
      terminal sequence of hTPO protein

<400> SEQUENCE: 2
atgaattctc acccttcctg agac                                             24

<210> SEQ ID NO 3
<211> LENGTH: 20
<212> TYPE: DNA
<213> ORGANISM: Artificial Sequence
<220> FEATURE:
<223> OTHER INFORMATION: Synthetic oligodeoxynucleotide primer 29-N

<400> SEQUENCE: 3
gctgtggtgt tgccctgtgg                                                  20

<210> SEQ ID NO 4
<211> LENGTH: 20
<212> TYPE: DNA
<213> ORGANISM: Artificial Sequence
<220> FEATURE:
<223> OTHER INFORMATION: Synthetic oligodeoxynucleotide primer 29-C

<400> SEQUENCE: 4
acagggcaac accacagctc                                                  20

<210> SEQ ID NO 5
<211> LENGTH: 22
<212> TYPE: DNA
<213> ORGANISM: Artificial Sequence
<220> FEATURE:
<223> OTHER INFORMATION: Synthetic oligodeoxynucleotide primer 30-N

<400> SEQUENCE: 5
gggttccgtt taaactctgc ag                                               22

<210> SEQ ID NO 6
<211> LENGTH: 24
<212> TYPE: DNA
<213> ORGANISM: Artificial Sequence
<220> FEATURE:
<223> OTHER INFORMATION: Synthetic oligodeoxynucleotide primer 30-C

<400> SEQUENCE: 6
ctgcagagtt taaacggaac ccag                                             24

```
<210> SEQ ID NO 7
<211> LENGTH: 24
<212> TYPE: DNA
<213> ORGANISM: Artificial Sequence
<220> FEATURE:
<223> OTHER INFORMATION: primer 31-N

<400> SEQUENCE: 7
agagggtgga attccctaca agca                                              24

<210> SEQ ID NO 8
<211> LENGTH: 24
<212> TYPE: DNA
<213> ORGANISM: Artificial Sequence
<220> FEATURE:
<223> OTHER INFORMATION: primer 31-C

<400> SEQUENCE: 8
tgcttgtagg gaattccacc ctct                                              24

<210> SEQ ID NO 9
<211> LENGTH: 18
<212> TYPE: DNA
<213> ORGANISM: Artificial Sequence
<220> FEATURE:
<223> OTHER INFORMATION: primer 32-N

<400> SEQUENCE: 9
gggcccggtt gacgcaga                                                     18

<210> SEQ ID NO 10
<211> LENGTH: 18
<212> TYPE: DNA
<213> ORGANISM: Artificial Sequence
<220> FEATURE:
<223> OTHER INFORMATION: primer 32-C

<400> SEQUENCE: 10
tctgcgtcaa ccgggccc                                                     18

<210> SEQ ID NO 11
<211> LENGTH: 25
<212> TYPE: DNA
<213> ORGANISM: Artificial Sequence
<220> FEATURE:
<223> OTHER INFORMATION: primer 33-N

<400> SEQUENCE: 11
ggactagaga cgtgttgctg gggac                                             25

<210> SEQ ID NO 12
<211> LENGTH: 25
<212> TYPE: DNA
<213> ORGANISM: Artificial Sequence
<220> FEATURE:
<223> OTHER INFORMATION: primer 33-C

<400> SEQUENCE: 12
gtccccagca acacgtctct agtcc                                             25

<210> SEQ ID NO 13
<211> LENGTH: 25
<212> TYPE: DNA
<213> ORGANISM: Artificial Sequence
<220> FEATURE:
<223> OTHER INFORMATION: primer 34-N
```

```
<400> SEQUENCE: 13
gaagcccaga tccgttagtt ctggc                                         25

<210> SEQ ID NO 14
<211> LENGTH: 25
<212> TYPE: DNA
<213> ORGANISM: Artificial Sequence
<220> FEATURE:
<223> OTHER INFORMATION: primer 34-C

<400> SEQUENCE: 14
gccagaacta acggatctgg gcttc                                         25

<210> SEQ ID NO 15
<211> LENGTH: 22
<212> TYPE: DNA
<213> ORGANISM: Artificial Sequence
<220> FEATURE:
<223> OTHER INFORMATION: primer 58-N

<400> SEQUENCE: 15
agctgtggtg tttggggccc gc                                            22

<210> SEQ ID NO 16
<211> LENGTH: 22
<212> TYPE: DNA
<213> ORGANISM: Artificial Sequence
<220> FEATURE:
<223> OTHER INFORMATION: primer 58-C

<400> SEQUENCE: 16
gcgggcccca aacaccacag ct                                            22

<210> SEQ ID NO 17
<211> LENGTH: 26
<212> TYPE: DNA
<213> ORGANISM: Artificial Sequence
<220> FEATURE:
<223> OTHER INFORMATION: primer 59-N

<400> SEQUENCE: 17
ctagagaggt gctgttgaca gctgtg                                        26

<210> SEQ ID NO 18
<211> LENGTH: 29
<212> TYPE: DNA
<213> ORGANISM: Artificial Sequence
<220> FEATURE:
<223> OTHER INFORMATION: primer 59-C

<400> SEQUENCE: 18
cacagctgtc aacagcagca cctctctag                                     29

<210> SEQ ID NO 19
<211> LENGTH: 28
<212> TYPE: DNA
<213> ORGANISM: Artificial Sequence
<220> FEATURE:
<223> OTHER INFORMATION: primer 60-N

<400> SEQUENCE: 19
ggtgggtggg gtccggttga cgcagagg                                      28

<210> SEQ ID NO 20
<211> LENGTH: 28
```

<212> TYPE: DNA
<213> ORGANISM: Artificial Sequence
<220> FEATURE:
<223> OTHER INFORMATION: primer 60-C

<400> SEQUENCE: 20
cctctgcgtc aaccggaccc cacccacc                                           28

<210> SEQ ID NO 21
<211> LENGTH: 27
<212> TYPE: DNA
<213> ORGANISM: Artificial Sequence
<220> FEATURE:
<223> OTHER INFORMATION: primer 61-N

<400> SEQUENCE: 21
tctgctgggg gaagcgttgg tgggtgg                                            27

<210> SEQ ID NO 22
<211> LENGTH: 27
<212> TYPE: DNA
<213> ORGANISM: Artificial Sequence
<220> FEATURE:
<223> OTHER INFORMATION: primer 61-C

<400> SEQUENCE: 22
ccacccacca acgcttcccc cagcaga                                            27

<210> SEQ ID NO 23
<211> LENGTH: 28
<212> TYPE: DNA
<213> ORGANISM: Artificial Sequence
<220> FEATURE:
<223> OTHER INFORMATION: primer 62-N

<400> SEQUENCE: 23
cagtgtgagg gttagattgg ttctgctg                                           28

<210> SEQ ID NO 24
<211> LENGTH: 28
<212> TYPE: DNA
<213> ORGANISM: Artificial Sequence
<220> FEATURE:
<223> OTHER INFORMATION: primer 62-C

<400> SEQUENCE: 24
cagcagaacc aatctaaccc tcacactg                                           28

<210> SEQ ID NO 25
<211> LENGTH: 22
<212> TYPE: DNA
<213> ORGANISM: Artificial Sequence
<220> FEATURE:
<223> OTHER INFORMATION: primer 63-N

<400> SEQUENCE: 25
cagtgtgagg tttagagagg tt                                                 22

<210> SEQ ID NO 26
<211> LENGTH: 22
<212> TYPE: DNA
<213> ORGANISM: Artificial Sequence
<220> FEATURE:
<223> OTHER INFORMATION: primer 63-C

<400> SEQUENCE: 26
aacctctcta aacctcacac tg                                            22

<210> SEQ ID NO 27
<211> LENGTH: 14
<212> TYPE: DNA
<213> ORGANISM: Artificial Sequence
<220> FEATURE:
<223> OTHER INFORMATION: synthetic oligodeoxynucleotide 1 of BamHI
      linker

<400> SEQUENCE: 27
cgcggatccg catg                                                     14

<210> SEQ ID NO 28
<211> LENGTH: 10
<212> TYPE: DNA
<213> ORGANISM: Artificial Sequence
<220> FEATURE:
<223> OTHER INFORMATION: synthetic oligodeoxynucleotide 1 of BamHI
      linker

<400> SEQUENCE: 28
cggatccgcg                                                          10

<210> SEQ ID NO 29
<211> LENGTH: 32
<212> TYPE: DNA
<213> ORGANISM: Artificial Sequence
<220> FEATURE:
<223> OTHER INFORMATION: KpnI-tagged primer corresponding to the N
      terminal sequence of hTPO protein

<400> SEQUENCE: 29
ggggtaccgc caccatggag ctgactgaat tg                                 32

<210> SEQ ID NO 30
<211> LENGTH: 332
<212> TYPE: PRT
<213> ORGANISM: Homo sapiens

<400> SEQUENCE: 30

Ser Pro Ala Pro Pro Ala Cys Asp Leu Arg Val Leu Ser Lys Leu Leu
 1               5                  10                  15

Arg Asp Ser His Val Leu His Ser Arg Leu Ser Gln Cys Pro Glu Val
                20                  25                  30

His Pro Leu Pro Thr Pro Val Leu Leu Pro Ala Val Asp Phe Ser Leu
            35                  40                  45

Gly Glu Trp Lys Thr Gln Met Glu Glu Thr Lys Ala Gln Asp Ile Leu
    50                  55                  60

Gly Ala Val Thr Leu Leu Leu Glu Gly Val Met Ala Ala Arg Gly Gln
65                  70                  75                  80

Leu Gly Pro Thr Cys Leu Ser Ser Leu Leu Gly Gln Leu Ser Gly Gln
                85                  90                  95

Val Arg Leu Leu Leu Gly Ala Leu Gln Ser Leu Leu Gly Thr Gln Leu
            100                 105                 110

Pro Pro Gln Gly Arg Thr Thr Ala His Lys Asp Pro Asn Ala Ile Phe
        115                 120                 125

Leu Ser Phe Gln His Leu Leu Arg Gly Lys Val Arg Phe Leu Met Leu
    130                 135                 140

Val Gly Gly Ser Thr Leu Cys Val Arg Arg Ala Pro Pro Thr Thr Ala
145                 150                 155                 160

-continued

```
Val Pro Ser Arg Thr Ser Leu Val Leu Thr Leu Asn Glu Leu Pro Asn
            165                 170                 175
Arg Thr Ser Gly Leu Leu Glu Thr Asn Phe Thr Ala Ser Ala Arg Thr
        180                 185                 190
Thr Gly Ser Gly Leu Leu Lys Trp Gln Gln Gly Phe Arg Ala Lys Ile
    195                 200                 205
Pro Gly Leu Leu Asn Gln Thr Ser Arg Ser Leu Asp Gln Ile Pro Gly
210                 215                 220
Tyr Leu Asn Arg Ile His Glu Leu Leu Asn Gly Thr Arg Gly Leu Phe
225                 230                 235                 240
Pro Gly Pro Ser Arg Arg Thr Leu Gly Ala Pro Asp Ile Ser Ser Gly
            245                 250                 255
Thr Ser Asp Thr Gly Ser Leu Pro Pro Asn Leu Gln Pro Gly Tyr Ser
        260                 265                 270
Pro Ser Pro Thr His Pro Pro Thr Gly Gln Tyr Thr Leu Phe Pro Leu
    275                 280                 285
Pro Pro Thr Leu Pro Leu Pro Val Val Gln Leu His Pro Leu Leu Pro
290                 295                 300
Asp Pro Ser Ala Pro Thr Pro Thr Pro Thr Ser Pro Leu Leu Asn Thr
305                 310                 315                 320
Ser Tyr Thr His Ser Gln Asn Leu Ser Gln Glu Gly
            325                 330
```

<210> SEQ ID NO 31
<211> LENGTH: 996
<212> TYPE: DNA
<213> ORGANISM: Artificial Sequence
<220> FEATURE:
<223> OTHER INFORMATION: cDNA sequence encoding hTPO mutein 40433

<400> SEQUENCE: 31

| | | |
|---|---|---|
| agcccggctc ctcctgcttg tgacctccga gtcctcagta aactgcttcg tgactcccat | 60 |
| gtccttcaca gcagactgag ccagtgccca gaggttcacc ctttgcctac acctgtcctg | 120 |
| ctgcctgctg tggactttag cttgggagaa tggaaaaccc agatggagga gaccaaggca | 180 |
| caggacattc tgggagcagt gacccttctg ctggagggag tgatggcagc acggggacaa | 240 |
| ctgggaccca cttgcctctc atccctcctg gggcagcttt ctggacaggt ccgtctcctc | 300 |
| cttgggccc tgcagagcct ccttggaacc cagcttcctc cacagggcag gaccacagct | 360 |
| cacaaggatc ccaatgccat cttcctgagc ttccaacacc tgctccgagg aaaggtgcgt | 420 |
| ttcctgatgc ttgtaggagg gtccacccic tgcgtcaggc gggccccacc caccacagct | 480 |
| gtccccagca cacgtctctc agtcctcaca ctgaacgagc tcccaaacag gacttctgga | 540 |
| ttgttggaga caaacttcac tgcctcagcc agaactactg gctctgggct tctgaagtgg | 600 |
| cagcagggat tcagagccaa gattcctggt ctgctgaacc aaacctccag gtccctggac | 660 |
| caaatccccg gatacctgaa caggatacac gaactcttga atggaactcg tggactcttt | 720 |
| cctggaccct cacgcaggac cctaggagcc ccggacattt cctcaggaac atcagacaca | 780 |
| ggctccctgc cacccaacct ccagcctgga tattctcctt ccccaaccca tcctcctact | 840 |
| ggacagtata cgctcttccc tcttccaccc accttgccca ccctgtggt ccagctccac | 900 |
| cccctgcttc ctgaccctc tgctccaacg cccaccccta ccagccctct tctaaacaca | 960 |
| tcctacaccc actcccagaa tctgtctcag gaaggg | 996 |

<210> SEQ ID NO 32

<211> LENGTH: 996
<212> TYPE: DNA
<213> ORGANISM: Artificial Sequence
<220> FEATURE:
<223> OTHER INFORMATION: cDNA sequence encoding hTPO mutein 40434

<400> SEQUENCE: 32

```
agcccggctc ctcctgcttg tgacctccga gtcctcagta aactgcttcg tgactcccat      60
gtccttcaca gcagactgag ccagtgccca gaggttcacc ctttgcctac acctgtcctg     120
ctgcctgctg tggactttag cttgggagaa tggaaaaccc agatggagga gaccaaggca     180
caggacattc tgggagcagt gacccttctg ctggagggag tgatggcagc acggggacaa     240
ctgggaccca cttgcctctc atccctcctg gggcagcttt ctggacaggt ccgtctcctc     300
cttggggccc tgcagagcct ccttggaacc cagcttcctc acagggcag accacagct      360
cacaaggatc ccaatgccat cttcctgagc ttccaacacc tgctccgagg aaaggtgcgt     420
ttcctgatgc ttgtaggagg gtccacccctc tgcgtcaggc gggcccccac caccacagct     480
gtccccagca gaacctctct agtcctcaca ctgaacgagc tcccaaacag gacttctgga     540
ttgttggaga caaacttcac tgcctcagcc agaactaacg gatctgggct tctgaagtgg     600
cagcagggat tcagagccaa gattcctggt ctgctgaacc aaacctccag gtccctggac     660
caaatccccg gatacctgaa caggatacac gaactcttga atggaactcg tggactcttt     720
cctggaccct cacgcaggac cctaggagcc ccggacattt cctcaggaac atcagacaca     780
ggctccctgc cacccaacct ccagcctgga tattctcctt ccccaaccca tcctcctact     840
ggacagtata cgctcttccc tcttccaccc accttgccca cccctgtggt ccagctccac     900
cccctgcttc ctgacccttc tgctccaacg cccaccccta ccagccctct tctaaacaca     960
tcctacaccc actcccagaa tctgtctcag gaaggg                               996
```

<210> SEQ ID NO 33
<211> LENGTH: 996
<212> TYPE: DNA
<213> ORGANISM: Artificial Sequence
<220> FEATURE:
<223> OTHER INFORMATION: cDNA sequence encoding hTPO mutein 40449

<400> SEQUENCE: 33

```
agcccggctc ctcctgcttg tgacctccga gtcctcagta aactgcttcg tgactcccat      60
gtccttcaca gcagactgag ccagtgccca gaggttcacc ctttgcctac acctgtcctg     120
ctgcctgctg tggactttag cttgggagaa tggaaaaccc agatggagga gaccaaggca     180
caggacattc tgggagcagt gacccttctg ctggagggag tgatggcagc acggggacaa     240
ctgggaccca cttgcctctc atccctcctg gggcagcttt ctggacaggt ccgtctcctc     300
cttggggccc tgcagagttt aaacggaacc cagcttcctc acagggcaa caccacagct     360
cacaaggatc ccaatgccat cttcctgagc ttccaacacc tgctccgagg aaaggtgcgt     420
ttcctgatgc ttgtaggagg gtccacccctc tgcgtcaggc gggcccccac caccacagct     480
gtccccagca acacgtctct agtcctcaca ctgaacgagc tcccaaacag gacttctgga     540
ttgttggaga caaacttcac tgcctcagcc agaactactg gctctgggct tctgaagtgg     600
cagcagggat tcagagccaa gattcctggt ctgctgaacc aaacctccag gtccctggac     660
caaatccccg gatacctgaa caggatacac gaactcttga atggaactcg tggactcttt     720
cctggaccct cacgcaggac cctaggagcc ccggacattt cctcaggaac atcagacaca     780
ggctccctgc cacccaacct ccagcctgga tattctcctt ccccaaccca tcctcctact     840
```

```
ggacagtata cgctcttccc tcttccaccc accttgccca ccctgtggt ccagctccac      900 cccctgcttc ctgacccttc tgctccaacg cccacccta ccagccctct tctaaacaca      960
tcctacaccc actcccagaa tctgtctcag gaaggg                               996
```

<210> SEQ ID NO 34
<211> LENGTH: 996
<212> TYPE: DNA
<213> ORGANISM: Artificial Sequence
<220> FEATURE:
<223> OTHER INFORMATION: cDNA sequence encoding hTPO mutein 40458

<400> SEQUENCE: 34

```
agcccggctc ctcctgcttg tgacctccga gtcctcagta aactgcttcg tgactcccat       60
gtccttcaca gcagactgag ccagtgccca gaggttcacc ctttgcctac acctgtcctg      120
ctgcctgctg tggactttag cttgggagaa tggaaaaccc agatggagga gaccaaggca      180
caggacattc tgggagcagt gaccttctg ctggagggag tgatggcagc acggggacaa       240
ctgggaccca cttgcctctc atccctcctg gggcagcttt ctggacaggt ccgtctcctc      300
cttgggggcc tgcagagcct ccttggaacc cagcttcctc cacagggcag gaccacagct      360
cacaaggatc ccaatgccat cttcctgagc ttccaacacc tgctccgagg aaaggtgcgt      420
ttcctgatgc ttgtaggagg gtccaccctc tgcgtcaggc gggccccaaa caccacagct      480
gtccccagca acacgtctct agtcctcaca ctgaacgagc tcccaaacag gacttctgga      540
ttgttggaga caaacttcac tgcctcagcc agaactactg gctctgggct tctgaagtgg      600
cagcagggat tcagagccaa gattcctggt ctgctgaacc aaacctccag gtccctggac      660
caaatccccg gatacctgaa caggatacac gaactcttga atggaactcg tggactcttt      720
cctggaccct cacgcaggac cctaggagcc ccggacattt cctcaggaac atcagacaca      780
ggctccctgc cacccaacct ccagcctgga tattctcctt ccccaaccca tcctcctact      840
ggacagtata cgctcttccc tcttccaccc accttgccca ccctgtggt ccagctccac      900 cccctgcttc ctgacccttc tgctccaacg cccacccta ccagccctct tctaaacaca      960
tcctacaccc actcccagaa tctgtctcag gaaggg                               996
```

HUMAN THROMBOPOIETIN COMPRISING GLYCOSYLATION SITED AT RESIDUES 157 AND 164

This application is a divisional of U.S. patent application No. 10,441,729, filed May 20, 2003, which is a divisional of U.S. patent application No. 09/720,410, filed Dec. 21, 2000, now abandoned, which application claims priority from Korean patent application numbers 1998-25935, filed Jun. 30, 1998, and 1999-25143, filed Jun. 29, 1999, the entire contents of each which are incorporated by reference herein.

FIELD OF THE INVENTION

The present invention relates to novel human thrombopoietin (hTPO) derivatives with high activities enhancing the platelet production in vivo, and to process of preparation thereof.

Particularly, this invention relates to novel hTPO derivatives wherein sugar chains are introduced by substituting amino acids such as asparagine for amino acids at specific positions in native hTPO; to nucleotide sequences encoding the hTPO derivatives; to expression vectors containing the nucleotide sequences; to process of construction thereof; to cell lines transformed with the vectors; and to process of preparing the hTPO derivatives thereby.

BACKGROUND

Thrombocytopenia is the disease of platelet deficiency caused by anticancer therapy, bone marrow graft and so on. In the process of anticancer therapy or bone marrow graft, megakaryocyte colony forming cells, the platelet precursor cells in bone marrow, are disrupted, and this leads to platelet deficiency. The thrombocytopenia patient is subject to bleeding in response to a light trauma, and more serious patient becomes bleeding without trauma. Bleeding is often fatal in this case since the blood is not stanched at all.

The current therapy for thrombocytopenia is nothing but the platelet transfusion. However, several problems and side effects are associated with this therapy, such as insufficient donors, transfusion-meditated infection with e.g. HIV (human immunodeficiency virus) and hepatitis viruses, the elicitation of immune response, and so on.

Platelet is a component of blood, originated from megakaryocyte precursor cells, and plays a role in the suppression of bleeding. Thrombopoietin (hereafter, referred to as "TPO"), a glycoprotein synthesized and secreted in liver or kidney, regulates the platelet level in blood. TPO accelerates the proliferation and differentiation of the megakaryocyte precursor cells, which is followed by the platelet production (Lok et al., Nature, 369: 565–568, 1994; De savage et al., Nature, 369: 533–568, 1994).

Since a gene encoding TPO was isolated first from human in 1994 (Lok et al., Nature, 369: 565–568, 1994; De savage et al., Nature, 369: 533–568, 1994; Miyazaki et al., Experimental hematol., 22: 838, 1994; WO 95/18858), clinical approaches for thrombocytopenia have been based on the function of human TPO (hereinafter, referred to as "hTPO"), that is, the regulation of the platelet level.

Three different approaches are proceeded in order to improve the activity of native hTPO.

Glycoprotein hTPO is expressed in cells as an inactive precursor comprising 353 amino acids, and the cleavage of signal peptide (21 amino acids) leads to the secretion of active hTPO protein (332 amino acids) out of the cells. The amino acid sequence of hTPO is divided into two regions. The N-terminal region comprising 151 amino acids contains catalytic site, and shows high similarity to that of erythropoietin (; EPO) The other region, C-terminal region is presumed to have a key role in the extracellular secretion and in vivo stability of hTPO.

The first method for modifying native hTPO relates to the deletion of the C-terminal region or the addition of new amino acids to the deleted hTPO.

In support of this approach, Amgen INC. developed various hTPO derivatives such as $hTPO_{151}$ (consisting of amino acids 1–151), $hTPO_{174}$ (consisting of amino acids 1–174) and the $hTPO_{163}$ supplemented with methionine-lysine in its N-terminal. However, these derivatives proved to show lower hTPO activity in vivo than native hTPO, although their activities were maintained in vitro (WO 95/26746, WO 95/25498).

In addition, Genentech INC. prepared from E. coli a recombinant $hTPO_{153}$ derivative having an N-terminal methionine (WO 95/18858). Kirin produced diverse hTPO derivatives with C-terminal deletion and $hTPO_{163}$ derivatives with substitution, deletion, or insertion at a specific amino acid residue (WO 95/21920). Other hTPO derivatives with C-terminal deletion were provided by Zymogenetics INC. (WO 95/21920; WO 96/17062) and G. D. Searl (WO 96/23888). These derivatives, however, failed to show higher activity of platelet production in vivo than native hTPO.

The second method is associated with the conjugation of polyethyleneglycol (; PEG) with hTPO fragment, which is exampled by $hTPO_{163}$-PEG of Amgen INC. (WO 95/26746).

The derivatives according to this method, however, have critical handicaps such as poor stability and safety, since they do not contain C-terminal region that is important for the stability of hTPO and since immune response may be elicited by the shift of their folding structures. Moreover, the qualities of products may be uneven because PEG is not so conjugated at a uniform proportion.

The third method exploits the glycosylation of hTPO, which may increase the hTPO activity.

Amgen INC. performed a mutagenesis where a specific nucleotide in cDNA encoding hTPO was substituted to bear amino acid sequence "Asn-X-Ser/Thr" (where X is any amino acid but proline). The mutated gene was used to prepare hTPO derivatives with C-terminal deletion, which comprised 174 amino acids and into which one or more N-linked glycosylation sites are produced (WO 96/25498).

Korea Research Institute of Biology and Biotechnology (KRIBB) produced a hTPO derivative where one sugar chain is incorporated into the intact native hTPO (Park et al., J. Biol. Chem., 273: 256–261, 1998), distinctive from the Amgen's partial hTPO derivatives.

However, all these derivatives did not show significantly higher levels of hTPO activity.

As described above, although various strategies have been employed to develop hTPO derivatives with enhanced biological activity, all failed to obtain the derivatives with higher in vivo hTPO activities than native hTPO.

Generally, numerous proteins exist as proteins adorned by oligosaccharide chains in specific position, i.e. glycoproteins. Two types of glycosylation have been found. In O-linked glycosylation, sugar chain is attached to the hydroxyl group of Ser/Thr residue in the glycoprotein. In N-linked glycosylation, sugar chain is attached to the amide group of "Asn-X-Ser/Thr" (X is any amino acid but proline).

The sugar chain in a glycoprotein exert various effects on the physical, chemical and biological properties such as protein stability and secretion, especially on the biological activity in vivo and pharmacokinetic properties (Jenkins et al., Nature Biotechnological., 14: 975–981, 1996; Liu et al., Act. TIBTECH., 10: 114–120, 1992).

These effects are exemplified by human interferon-γ and glucose transport protein, where amino acid substitution at proper glycosylation site gave rise to the striking decrease in the hTPO activity, suggesting that N-linked sugar chain may have significant effects on the activity of the glycoprotein (Sareneva et al., Biochem. J. 303: 831–840, 1994; Asano et al., FEBS, 324: 258–261, 1993).

However, the introduction of additional sugar chains is not always accompanied with an increase in the catalytic activity of the glycoprotein, as described in the precedent art of Amgen INC. and KRIBB (WO 96/25498; Park et al., J. Biol. Chem., 273: 256–261, 1993). Although additional sugar chains were introduced into these hTPO derivatives, the biological activities of the glycoproteins were rather reduced when compared with native hTPO. According to this observation, it is not the number of sugar chains but the specific glycosylation site that is crucial for elevating its catalytic activity.

We, the inventors of this invention, have prepared various hTPO derivatives and examined their activities. This invention is performed by disclosing that several hTPO derivatives such as derivative wherein Asn is substituted for $Arg^{164}$; derivative wherein Asn is substituted for $Thr^{193}$; derivative wherein Asn is substituted for $Pro^{157}$ and $Arg^{164}$; and derivative wherein Asn is substituted for $Leu^{108}$, $Arg^{117}$ and $Arg^{164}$ produce the remarkably higher levels of platelets than native hTPO does, which is not ever observed in the current hTPO derivatives.

SUMMARY OF THE INVENTION

It is an object of this invention to provide novel hTPO derivatives that show the higher activities enhancing the platelet production in vivo than native hTPO does.

In accordance with the present invention, the foregoing objects and advantages are readily obtained.

The present invention provides novel hTPO derivatives with higher activity inducing the platelet production in vivo. Additional sugar chains are introduced into said hTPO derivatives through substituting amino acids such as asparagine for amino acids at specific positions in native hTPO.

This invention also provides genes encoding said hTPO derivatives.

In addition, this invention provides process of preparing said hTPO derivatives, comprising the step wherein said genes are inserted into appropriate vector; the step wherein a host cell is transfected with said vector; and the step wherein the transfected cells are cultured in appropriate medium.

Further features of the present invention will appear hereinafter.

DETAILED DESCRIPTION OF PREFERRED EMBODIMENTS

Hereinafter, the present invention is described in detail.

The present invention provides novel hTPO derivatives with enhanced activity inducing the platelet production in vivo. Additional sugar chains are introduced into said hTPO derivatives through substituting amino acids such as asparagine for amino acids at specific positions in native hTPO.

To develop novel hTPO derivatives with enhanced activity inducing the platelet production in vivo, a variety of hTPO derivatives were prepared, into which one or more sugar chains are introduced through substituting one or more amino acids at specific positions in a hTPO protein. In result, N-linked glycosylation site "Asn-X-Ser/Thr" (where X is any amino acid but proline) is created at the specific positions.

In a preferred embodiment, site-specific mutagenesis using overlap PCR (Cheng et al., Proc. Natl. Acad. Soc. USA, 91: 5695, 1994) was employed to produce the genes encoding hTPO derivatives with specific amino acids substituted at specific position (see FIG. 1).

First, the following primer pairs containing mutated sequences were synthesized chemically. These oligonucleotide primer pairs contain the nucleotide sequences corresponding to the mutated amino acid residues, and extend to the 5' or 3' neighboring sequence to the mutated region in hTPO cDNA.

where the two overlap PCR products were employed as a template and two oligonucleotides (SEQ ID NO: 1 and NO: 2) were employed as PCR primers.

Figure 1:
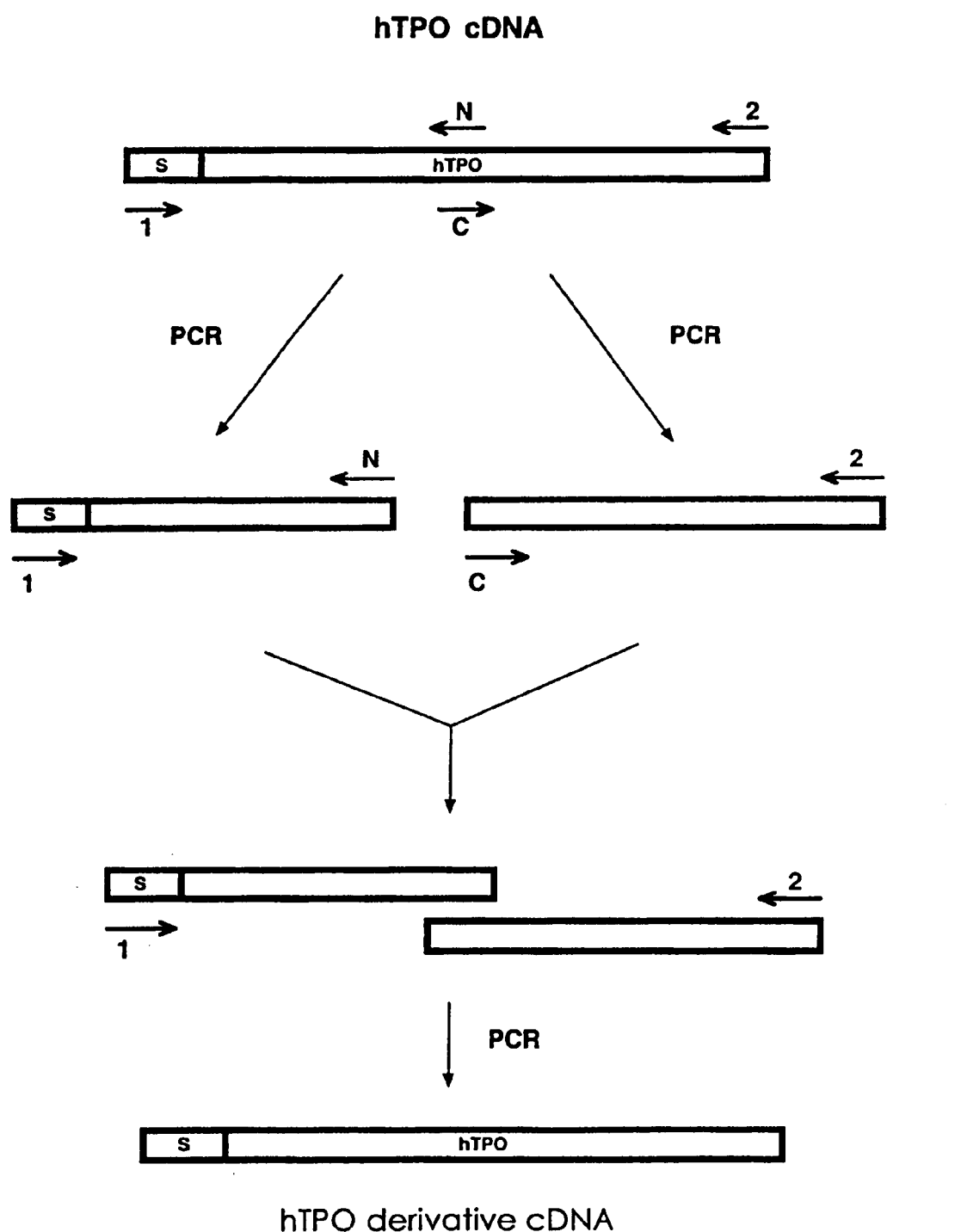
FIG. 1 depicts PCR-based mutagenesis wherein the cDNAs encoding hTPO derivatives are produced, where
1: primer described by SEQ ID NO: 1;
2: primer described by SEQ ID NO: 2;
N: N-primer;
C: C-primer;
S: signal sequence.

Through aforesaid processes, 1078-bp full-length cDNA sequences encoding hTPO derivatives were prepared, which contained a variety of mutated sequences (see FIG. 1).

TABLE 1

Primer pairs for site-specific mutagenesis

| Derivative | primer | SEQ ID NO: | Nucleotide sequence |
|---|---|---|---|
| 40429 | 29-N | 3 | 5'-GCTGT GGTGT TGCCC TGTGG-3' |
|  | 29-C | 4 | 5'-ACAGG GCAAC ACCAC AGCTC-3' |
| 40430 | 30-N | 5 | 5'-GGGTT CCGTT TAAAC TCTGC AG-3' |
|  | 30-C | 6 | 5'-CTGCA GAGTT TAAAC GGAAC CCAG-3' |
| 40431 | 31-N | 7 | 5'-AGAGG GTGGA ATTCC CTACA AGCA-3' |
|  | 31-C | 8 | 5'-TGCTT GTAGG GAATT CCACC CTCT-3' |
| 40432 | 32-N | 9 | 5'-GGGCC CGGTT GACGC AGA-3' |
|  | 32-C | 10 | 5'-TCTGC GTCAA CCGGG CCC-3' |
| 40433 | 33-N | 11 | 5'-GGACT AGAGA CGTGT TGCTG GGAC-3' |
|  | 33-C | 12 | 5'-GTCCC CAGCA ACACG TCTCT AGTCC-3' |
| 40434 | 34-N | 13 | 5'-GAAGC CCAGA TCCGT TAGTT CTGGC-3' |
|  | 34-C | 14 | 5'-GCCAG AACTA ACGGA TCTGG GCTTC-3' |
| 40458 | 58-N | 15 | 5'-AGCTG TGGTG TTTGG GGCCC GC-3' |
|  | 58-C | 16 | 5'-GCGGG CCCCA AACAC CACAG CT-3' |
|  | 33-N | 11 | 5'-GGACT AGAGA CGTGT TGCTG GGAC-3' |
|  | 33-C | 12 | 5'-GTCCC CAGCA ACACG TCTCT AGTCC-3' |
| 40459 | 59-N | 17 | 5'-CTAGA GAGGT GCTGT TGACA GCTGT G-3' |
|  | 59-C | 18 | 5'-CACAG CTGTC AACAG CAGCA CCTCT CTAG-3' |
| 40460 | 60-N | 19 | 5'-GGTGG GTGGG GTCCG GTTGA CGCAG AGG-3' |
|  | 60-C | 20 | 5'-CCTCT GCGTC AACCG GACCC CACCC ACC-3' |
|  | 33-N | 11 | 5'-GGACT AGAGA CGTGT TGCTG GGAC-3' |
|  | 33-C | 12 | 5'-GTCCC CAGCA ACACG TCTCT AGTCC-3' |
| 40461 | 61-N | 21 | 5'-TCTGC TGGGG GAAGC GTTGG TGGGT GG-3' |
|  | 61-C | 22 | 5'-CCACC CACCA ACGCT TCCCC CAGCA GA-3' |
|  | 33-N | 11 | 5'-GGACT AGAGA CGTGT TGCTG GGAC-3' |
|  | 33-C | 12 | 5'-GTCCC CAGCA ACACG TCTCT AGTCC-3' |
| 40462 | 62-N | 23 | 5'-CAGTG TGAGG GTTAG ATTGG TTCTG CTG-3' |
|  | 62-C | 24 | 5'-CAGCA GAACC AATCT AACCC TCACA CTG-3' |
| 40463 | 63-N | 25 | 5'-CAGTG TGAGG TTTAC AGAGG TT-3' |
|  | 63-C | 26 | 5'-AACCT CTCTA AACCT CACAC TG-3' |
|  | 33-N | 11 | 5'-GGACT AGAGA CGTGT TGCTG GGAC-3' |
|  | 33-C | 12 | 5'-GTCCC CAGCA ACACG TCTCT AGTCC-3' |

Overlap PCR was performed wherein the established vector pBlue404 (KOREA APPLICATION NO. 97-7512) containing hTPO cDNA was employed as a template. On the one hand, the oligonucleotide (SEQ ID NO: 1) encoding hTPO signal peptide and one of oligonucleotides (N-primer series in Table 1) encoding mutated sequences were employed as PCR primers. On the other hand, the oligonucleotide (SEQ ID NO: 2) containing hTPO C-terminal ORF and stop codon and one of oligonucleotides (C-primer series in Table 1) encoding mutated sequences were employed as PCR primers.

The overlap PCR products contain the DNA sequences covering from N-terminal signal sequence to mutated region and the DNA sequences covering from mutated region to C-terminal region, respectively.

To obtain the full-length hTPO cDNA sequence containing the target site for amino acid substitution, PCR was done In a further embodiment, vectors containing the cDNAs for hTPO derivatives were constructed in order to obtain the expression vectors containing the cDNAs and finally to produce the cell lines transfected with the expression vectors.

Particularly, the established vector pBlueBac4 and each cDNA encoding hTPO derivative were digested with BglII and EcoRI restriction enzymes, respectively. Then the two DNA fragments were linked with T4 DNA ligase to construct vectors containing the hTPO derivative cDNA (see FIG. 2).

The resulting vectors are illustrated by Table 2, which gives the names of the vectors, the mutated sequences encoding hTPO derivatives, and the amino acid residues modified in accordance with the mutation.

The amino acid sequences of hTPO derivatives of this invention are represented by a method where they are described with the amino acid residue substituted and a specified position in the amino acid sequence of native hTPO (SEQ ID NO: 30). For instance, a hTPO derivative of this invention, 40430, may be also referred to as "[Asn$^{108}$] hTPO" corresponding to the amino acid sequence described by SEQ ID NO: 30, except for asparagine substituted for the amino acid residue 108.

TABLE 2

The substituted amino acid and nucleotide sequences in the vectors containing hTPO derivative cDNAs

| Vectors | substituted amino acid | Mutated nucleotide |
|---|---|---|
| pBlue 29 | $R^{117} \rightarrow N^{117}$ | AGG → AAC |
| pBlue 30 | $L^{108} \rightarrow n^{108}$ | CTT → AAT |
| pBlue 31 | $G^{146}G^{147} \rightarrow G^{146}G^{147}$ | GGAGGG → GGGAAT |
| pBlue 32 | $R^{153} \rightarrow N^{153}$ | AGG → AAC |
| pBlue 33 | $R^{164}T^{165} \rightarrow n^{164}T^{165}$ | AGAACC → AACACG |
| pBlue 34 | $T^{193}G^{194} \rightarrow N^{193}G^{194}$ | ACTGGT → AACGGA |
| pBlue 58 | $P^{157} \rightarrow N^{157}$ $R^{164}T^{165} \rightarrow N^{164}T^{165}$ | CCC → AAC AGAACC → AACACG |
| pBlue 59 | $R^{162}, R^{164} \rightarrow N^{162}, S^{164}$ | CCC, AGA → AAC, AGC |

TABLE 2-continued

The substituted amino acid and nucleotide sequences in the vectors containing hTPO derivative cDNAs

| Vectors | substituted amino acid | Mutated nucleotide |
|---|---|---|
| pBlue 60 | $R^{153}, A^{155} \rightarrow N^{153}, T^{155}$ $R^{164}T^{165} \rightarrow N^{164}T^{165}$ | AGG, GCC → AAC, ACC AGAACC → AACACG |
| pBlue 61 | $T^{159}, V^{161} \rightarrow N^{159}, S^{161}$ | ACA, GTC → AAC, TCC |
| pBlues 62 | $S^{166}, V^{168} \rightarrow N^{166}, T^{168}$ | TCT, GTC → AAT, ACC |
| pBlue 63 | $R^{164}T^{165} \rightarrow N^{164}T^{165}$ $V^{168} \rightarrow N^{168}$ | AGAACC → AACACG GTC → AAC |

In another preferred embodiment, the expression vectors, which contain the hTPO derivative cDNA sequences, were constructed in order to be introduced into an animal cells.

Figure 3:
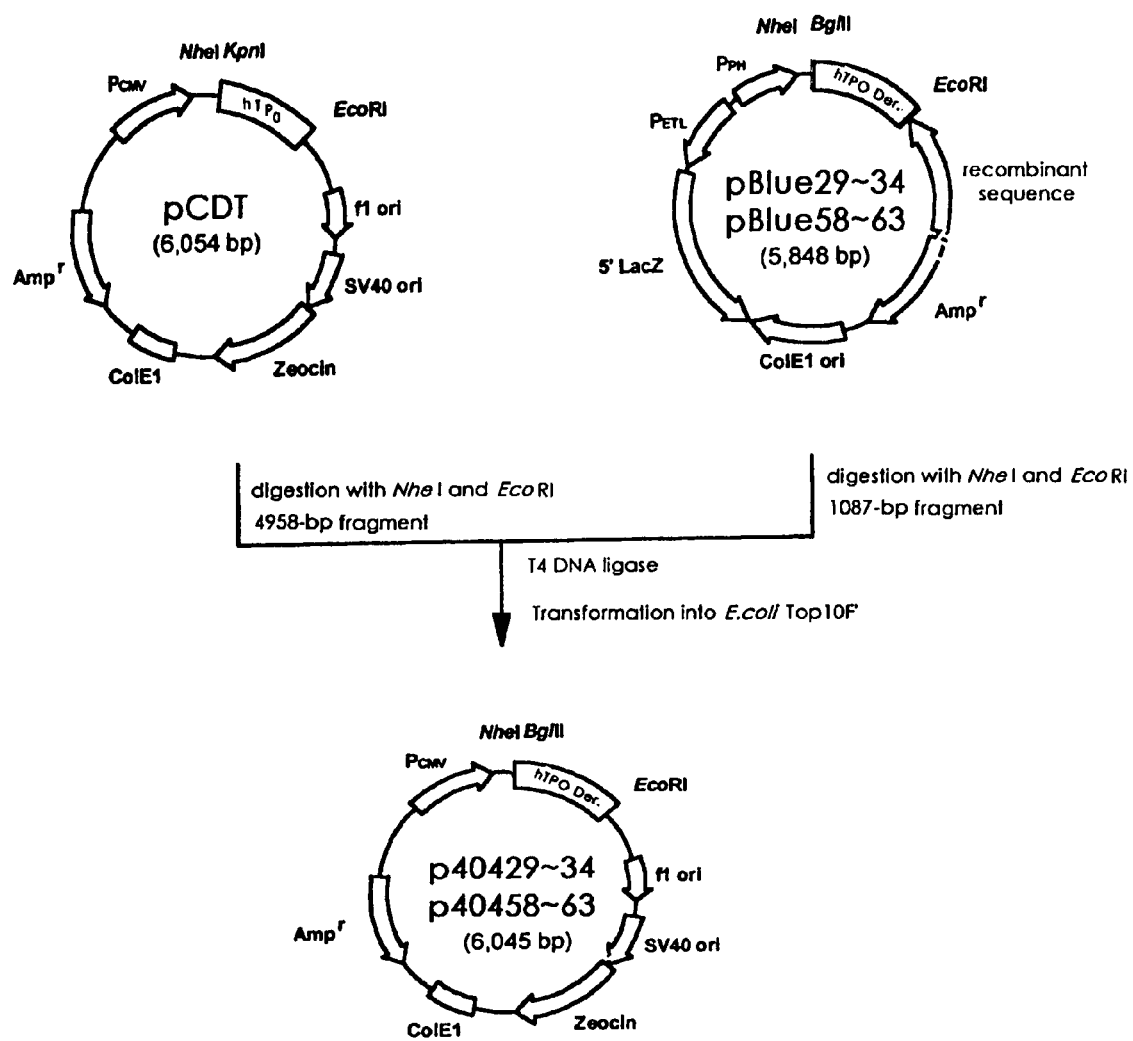
FIG. 3 depicts the process of constructing animal expression vectors that the mutated cDNAs are subcloned in pCDT vector.

Specifically, pCDT vector was prepared through the insertion of native hTPO cDNA into the established vector pCDNA3.1. The pCDT and the vectors containing hTPO derivative genes, such as pBlue29, pBlue30, pBlue31, pBlue32, pBlue33, pBlue34, pBlue58, pBlue59, pBlue60, pBlue61, pBlue62 and pBlue63 were digested with NheI and EcoRI enzymes. Then, these fragments were ligated with T4 DNA ligase to obtain animal expression vector containing each hTPO derivative gene (see FIG. 3 and Table 3).

TABLE 3

The substituted amino acid and nucleotide sequences in animal expression vectors containing hTPO derivative cDNAs.

| Expression vector | Mutated amino acid | Mutated base |
|---|---|---|
| p40429 | $R^{117} \rightarrow N^{117}$ | AGG → AAC |
| p40430 | $L^{108} \rightarrow N^{108}$ | CTT → AAT |
| p40431 | $G^{146}G^{147} \rightarrow G^{146}N^{147}$ | GGAGGG → GGGAAT |
| p40432 | $R^{153} \rightarrow N^{153}$ | AGG → AAC |
| p40433 | $R^{164}T^{165} \rightarrow N^{164}T^{165}$ | AGAACC → AACACG |
| p40434 | $T^{193}G^{194} \rightarrow N^{193}G^{194}$ | ACTGGT → AACGGA |
| p40435 | p40429 + p40431 | |
| p40436 | p40429 + p40433 | |
| p40437 | p40430 + p40431 | |
| p40438 | p40430 + p40433 | |
| p40439 | p40431 + p40433 | |
| p40446 | p40429 + p40431 + p40433 | |
| p40447 | p40430 + p40431 + p40433 | |
| p40449 | p40429 + p40430 + p40433 | |

TABLE 3-continued

The substituted amino acid and nucleotide sequences in animal expression vectors containing hTPO derivative cDNAs.

| Expression vector | Mutated amino acid | Mutated base |
|---|---|---|
| p40458 | $P^{157} \rightarrow N^{157}$<br>$R^{164}T^{165} \rightarrow N^{164}T^{165}$ | CCC $\rightarrow$ AAC<br>AGAACC $\rightarrow$ AACACG |
| p40459 | $R^{162}, R^{164} \rightarrow N^{162}, S^{164}$ | CCC, AGA $\rightarrow$ AAC, AGC |
| p40460 | $R^{153}, A^{155} \rightarrow N^{153}, T^{155}$<br>$R^{164}T^{165} \rightarrow N^{164}T^{165}$ | AGC, GCC $\rightarrow$ AAC, ACC<br>AGAACC $\rightarrow$ AACACG |
| p40461 | $T^{159}, V^{161} \rightarrow N^{159}, S^{161}$<br>$R^{164}T^{165} \rightarrow N^{164}T^{165}$ | ACA, GTC $\rightarrow$ AAC, TCC<br>AGAACC $\rightarrow$ AACACG |
| p40462 | $S^{166}, V^{168} \rightarrow N^{166}, T^{168}$ | TCT, GTC $\rightarrow$ AAT, ACC |
| p40463 | $R^{164}T^{165} \rightarrow N^{164}T^{165}$<br>$V^{168} \rightarrow N^{168}$ | AGAACC $\rightarrow$ AACACG<br>GTC $\rightarrow$ AAC |

The scope of this invention includes not only DNA sequences of Table 3 but also other DNA sequences corresponding to the amino acid sequences of Table 3, based on the degeneracy of genetic code. In other words, all of DNA sequences encoding hTPO derivatives that contain the modified amino acids of Table 3 may be employed as a mutant hTPO gene.

For example, a hTPO derivative, which may be prepared from an expression vector p40433, includes a polypeptide [$Asn^{164}$] hTPO, which may be encoded not only by DNA sequence of SEQ ID NO: 31 but also by degenerate DNA sequences.

To confirm the insertion of mutated sequences into the vector, the DNA sequencing of PCR products may be employed. Alternatively, if the overlap PCR primers are designed to contain a new restriction site or to delete a wild-type restriction site, the restriction map of the vector may be used to examine mutagenesis. If an expression vector p40433, for example, has a mutated sequence ACACGT in place of wild-type sequence GAACCT, AflIII restriction site will be created in p40433. Thus, the digestion of p40433 with AflIII can be used to confirm the introduction of mutated sequence.

In a preferred embodiment, hTPO derivatives with two or more amino acid modifications were produced using said expression vectors in order to attach additional sugar chains to the modified amino acid of native hTPO.

Particularly, two kinds of said expression vectors were digested with appropriate restriction enzymes, and then the resulting fragments were subcloned in said pCDT vector to construct expression vectors which contain the hTPO derivative genes with two or three regions modified. For example, an expression vector p40429 was digested with NheI and BspMI enzymes to obtain a DNA fragment involved in the amino acid substitution $Arg^{117} \rightarrow Asn^{117}$. In addition, an expression vector p40431 was digested with BspMI and Bsu36I enzymes to obtain a DNA fragment involved in the amino acid substitution $Gly^{147} \rightarrow Asn^{147}$. The resulting two DNA fragments were inserted into the BspMI-Bsu36I site of the pCDT vector, constructing an expression vector p40435 that contained a DNA sequence encoding hTPO with two amino acid substitutions, $Arg^{117} \rightarrow Asn^{117}$ and $Gly^{147} \rightarrow Asn^{147}$. In accordance with this procedure, expression vectors such as p40436, p40437, p40438, p40439, p40446, p40447, p40448, and p40449 were constructed (see Table 3).

In a further preferred embodiment, animal cell transformants expressing each hTPO derivative was prepared.

Particularly, said expression vectors were transfected to animal cell line CHO/K-1 through the lipofectamin method, preparing animal cell line expressing each hTPO derivative.

According to the name of the expression vector introduced, the transfected lines were designated CHO K-1/p40429, CHO K-1/p40430, CHO K-1/p40431, CHO K-1/p40432 etc., and CHO K-1/p40433 was deposited in Korean Collection for Type Cultures (; KCTC) on Jun. 17, 1998 (Accesion NO: KCTC 0495BP).

In another preferred embodiment, hTPO derivatives were prepared, by culturing animal cell lines transfected with the expression vector of this invention.

Particularly, the transfected lines were subcultured in a serum-containing medium on large scale, and then transferred to a secretion medium. Cultured medium was concentrated and dialyzed to obtain hTPO derivatives.

A hTPO derivative isolated from CHO K-1/p40433 is polypeptide [$Asn^{164}$] hTPO where asparagine is substituted for $Arginine^{164}$ in native hTPO sequence.

A hTPO derivative isolated from CHO K-1/p40434 is polypeptide [$Asn^{193}$] hTPO where Asn is substituted for $threonine^{193}$ in native hTPO sequence.

A hTPO derivative isolated from CHO K-1/p40449 is polypeptide [$Asn^{108}$, $Asn^{117}$, $Asn^{164}$] hTPO where asparagine is substituted for $leucine^{108}$, $arginine^{117}$ and $arginine^{164}$ in native hTPO sequence.

A hTPO derivative isolated from CHO K-1/p40458 is polypeptide [$Asn^{157}$, $Asn^{164}$] hTPO where asparagine is substituted for $proline^{157}$ and $arginine^{164}$ in native hTPO sequence.

In accordance with the names of expression vectors, the hTPO derivatives expressed in the animal cells were designated 40429 to 40439, 40446, 40447, 40449, and 40458 to 40463, respectively. Their in vitro activities were estimated by measuring proliferation of megakaryocyte leukemia cell line.

Figure 4:
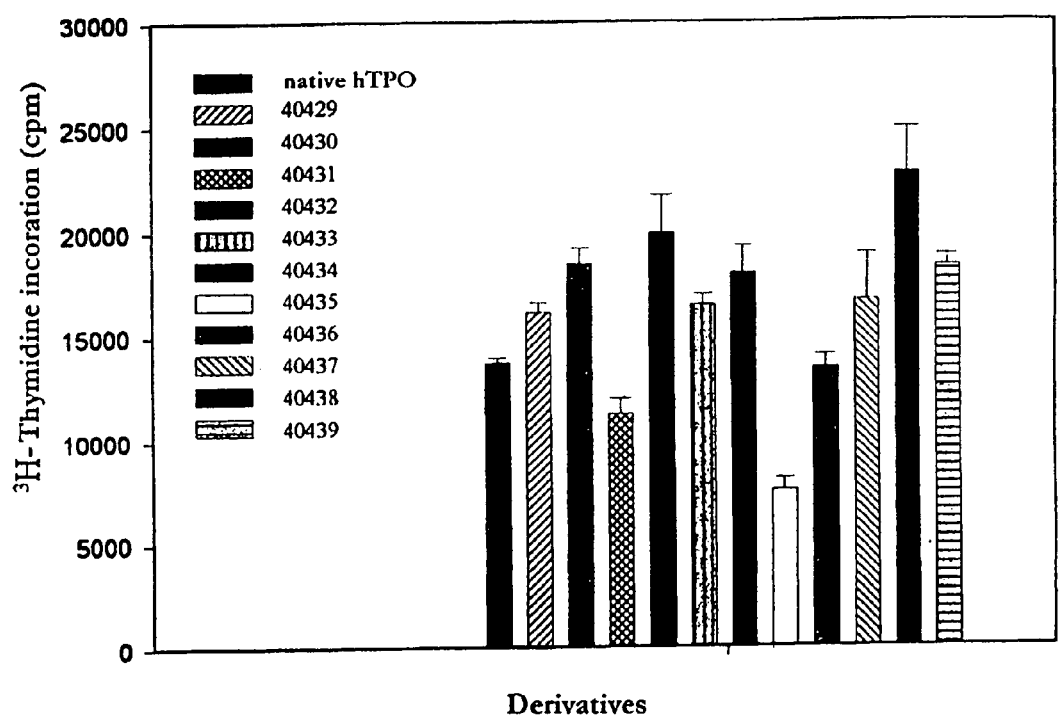
FIG. 4 presents the result of cell proliferation assay where the activity of M-07e cell proliferation is measured in the presence of hTPO derivatives expressed in animal cells.

In result, derivatives such as 40429, 40430, 40432, 40433, 40434, 40437, 40438, 40439, and the like showed higher levels of biological activity than native hTPO did. No significant relationship between the numbers of additional sugar chains and the in vitro activities was observed, since activities were increased or decreased regardless of the number of sugar chains introduced (see FIG. 4).

In a preferred embodiment, hTPO derivatives were administered to mouse and then platelet levels were measured in order to investigate the in vivo biological activities of the hTPO derivatives.

In detail, 8-week-old mice were divided into 4~5 groups according to their weight and then a predetermined concentration of hTPO was subcutaneously administered to mice. After administration, blood was collected from peripheral vessels of the mice, and platelet levels in blood were measured. While most of derivatives were found to show lower platelet levels than native hTPO did, derivatives 40433, 40434, 40449 and 40458 produced platelets at similar or higher efficiencies (see FIG. 6, 7a, or 7b).

These results suggested that hTPO activity in vivo is dependent not on the number of introduced sugar chains but on the specific position of sugar chains. That is, in order to increase the in vivo activity of hTPO, sugar chains should be introduced into specific positions in hTPO, such as amino acid 164, amino acid 193, and so on.

Most notably, platelet levels in 40433-treated group were higher than in native hTPO-treated group, for 2 days from day 3 or 4 after administration, demonstrating that 40433 can be used as a therapeutic agent of thrombocytopenia. The maximum platelet levels in 40433-treated mice were observed on day 5 after administration, reaching 134% of native hTPO activity on day 5, and more than 180% in total.

In another aspect of this invention, in vivo hTPO activities were investigated in purified hTPO derivatives that had produced same or higher platelet levels than native hTPO. To do this, dhfr expression vectors containing the hTPO derivative genes were constructed, and the resulting vectors were used to prepare cell lines expressing hTPO genes efficiently.

Figure 8:
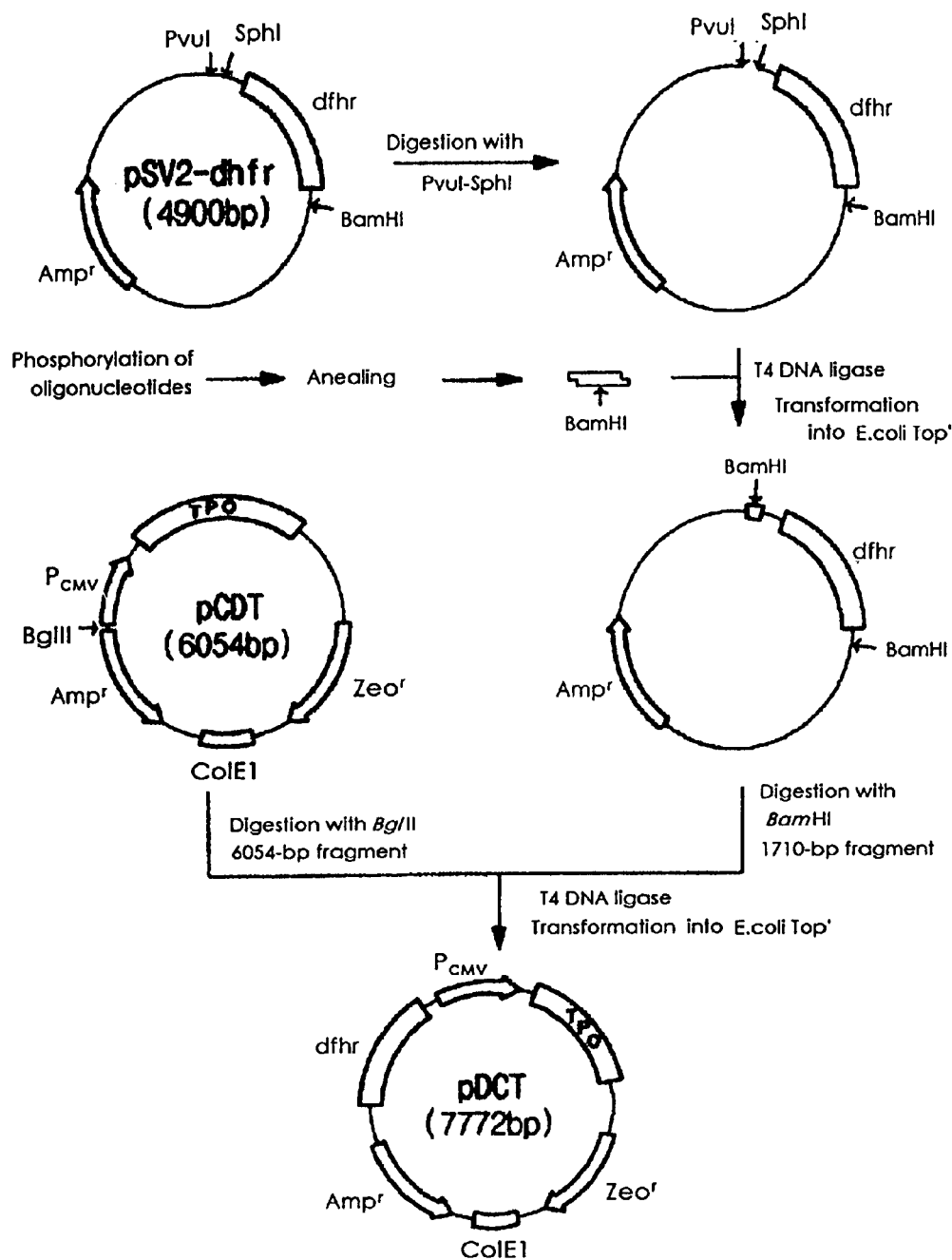
FIG. 8 depicts the process of constructing the dhfr expression vectors that contain a gene encoding native hTPO or hTPO derivatives.

Particularly, BamHI linker was connected to the PvuII-SphI fragment of pSV2-dhfr vector containing dfhr gene. This 1710-bp DNA fragment containing dhfr gene was inserted into pCDT to prepare dhfr expression vector pDCT containing native hTPO gene. Then, the hTPO derivative genes were inserted into pDCT in place of native hTPO gene, constructing dhfr expression vectors pD40433, pD40434, pD40449, and pD40458 (see FIG. 8).

The dhfr expression vectors containing hTPO derivative genes can be readily amplified in the genome of the transfected eukaryotic cells by subculturing the cells. In a preferred embodiment, these vectors were transfected into animal cell line CHO/dhfr(-). The novel transfected cell lines were designated CHO dhfr-/pD40433, CHO dhfr-/pD40434, CHO dhfr-/pD40449, and CHO dhfr-/pD40458, respectively. CHO dhfr-/pD40434, CHO dhfr-/pD40449, and CHO dhfr-/pD40458 were deposited in Korean Collection for Type Cultures (; KCTC) on Jun. 8, 1999 (Accession NO: KCTC 0630BP, KCTC 0631BP, KCTC 0632BP, respectively). Other dhfr vectors containing hTPO derivative genes and its transfected cell lines may be obtained according to the said procedure.

Figure 9:
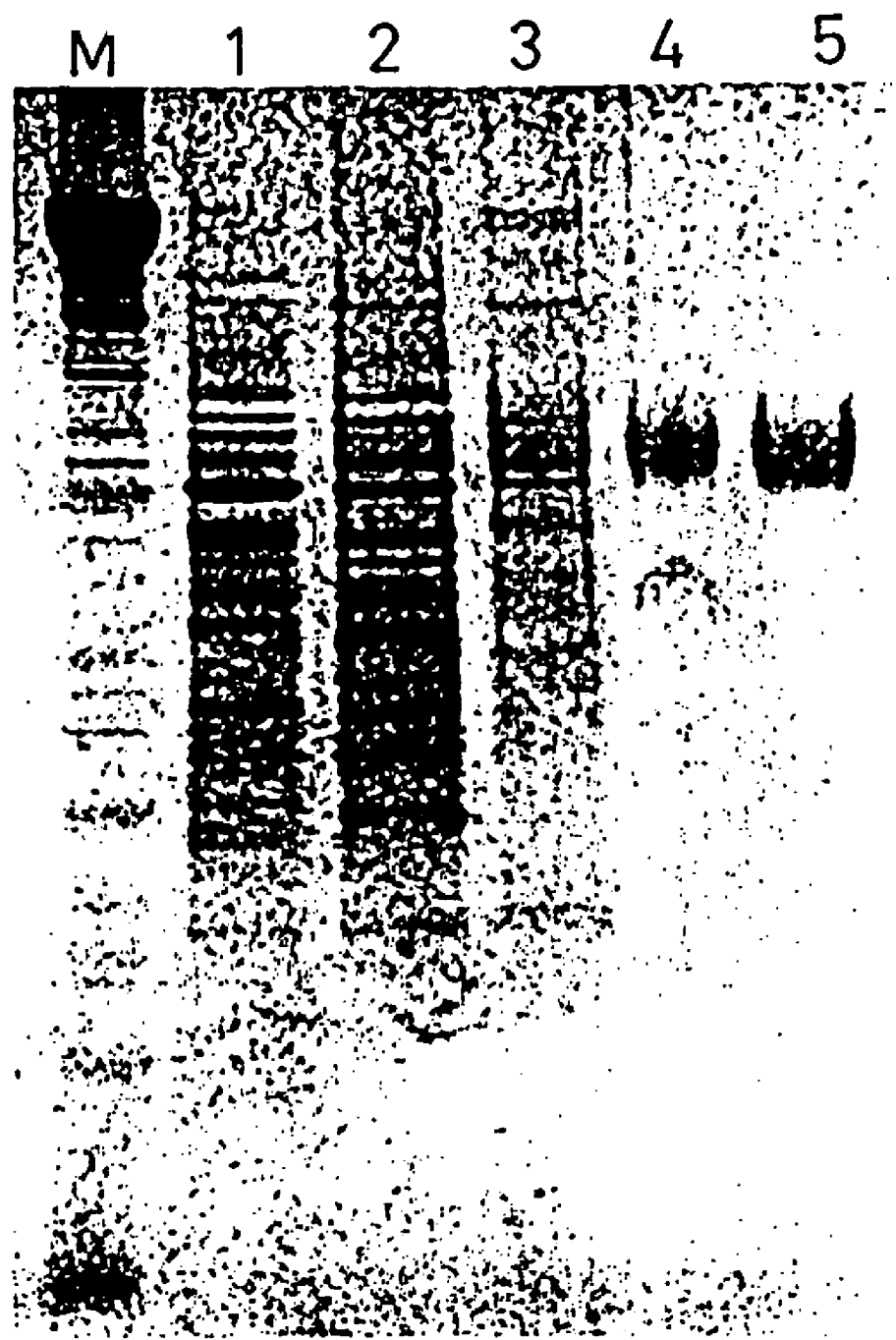
FIG. 9 presents the result of SDS-PAGE and silver staining with the various fractions obtained in the purification of a hTPO derivative, where
lane M: size marker;
lane 1: culture supernatant;
lane 2: CM-ion exchange affinity column elutes;
lane 3: phenylsephrose column elutes;
lane 4: hydroxyapatite column elutes;
lane 5: Q cartridge column elutes.

The transfected cell lines can be cultured on large scale, and hTPO derivatives can be purified in accordance with the established methods. Various column chromatography procedures may be employed to purify hTPO derivatives from cell lines that are transfected with dhfr expression vectors containing said hTPO derivative genes. In a preferred embodiment, CM ion-exchange affinity column, phenyl sepharose column, hydroxylapatite column, and so on were employed (see FIG. 9).

Figure 10:
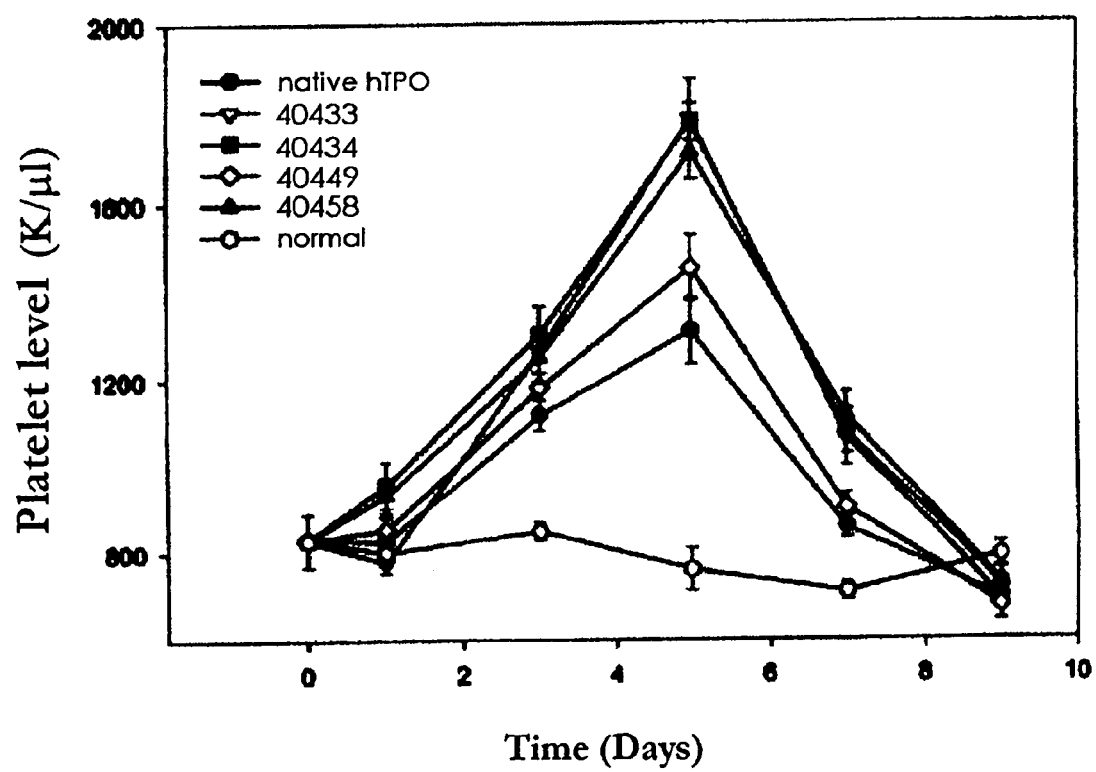
FIG. 10 presents the in vivo activities of native hPO and various hTPO derivatives, which are determined by measuring the number of platelets in mouse blood after treatment with native hTPO or purified hTPO derivatives (10 μg/kg).

To evaluate the in vivo biological activities of the purified hTPO derivatives, platelet levels were measured according to said process, after the derivatives were administered to mice. In 40433-, 40434-, 40449- and 40458-treated groups, the platelet yields reached 177%, 191%, 126% and 179% of native hTPO-treated group, respectively, for 10 days since the administration (see FIG. 10).

To confirm the introduction of additional sugar chains into hTPO derivatives, SDS-PAGE and subsequent Western blot analysis were performed with the purified native hTPO and hTPO derivatives. In result, the molecular weights of derivatives 40433 and 40434 were larger than that of native hTPO. The molecular weights of 40458 with two additional sugar chains and 40449 with three ones were proportionally increased, depending on the number of sugar chains (see FIG. 11).

Figure 12A:
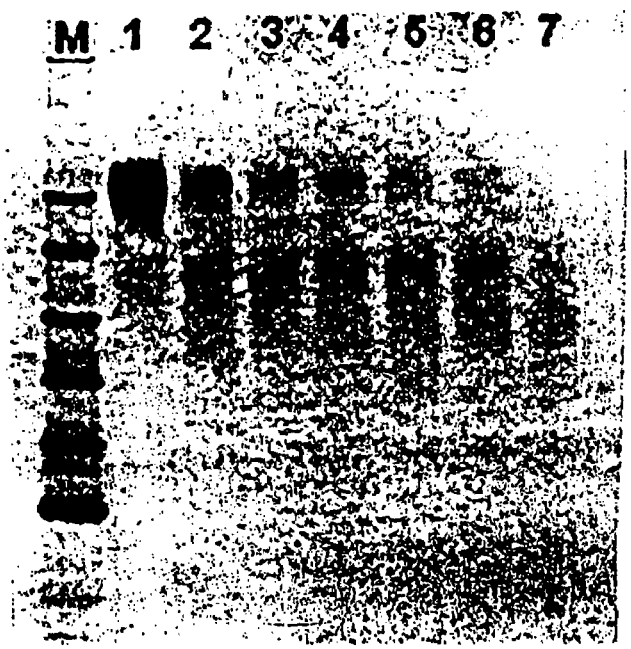
FIGS. 12a and 12b present the result of Western blot analysis, in which the thrombin-digestion pattern of native hTPO (FIG. 12a) or its derivative 40433 (FIG. 12b) is shown according to the time after digestion, where
lane M: size marker;
lane 1: Before digestion;
lane 2: 30 minutes after digestion;
lane 3: 1 hour;
lane 4: 2 hours;
lane 5: 3 hours;
lane 6: 4 hours;
lane 7: 6 hours.
Figure 12B:
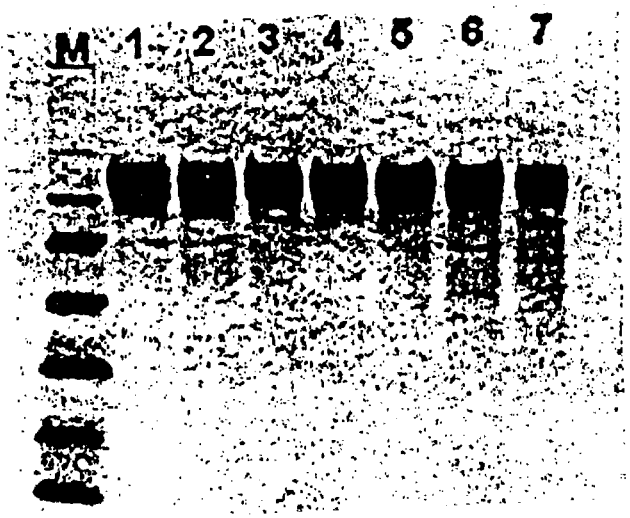

To examine the stability of hTPO derivatives, native hTPO and a derivative 40433 were treated with thrombin, and then the protein bands in Western blot were observed in accordance with the digestion time. In result, 40433 was more stable against digestion with thrombin than native hTPO (see FIG. 12). Thus, it was suggested that increased stability due to glycosylation might contribute to the elevation of in vivo hTPO activity.

The pharmaceutical composition containing the hTPO derivatives of this invention may be prepared in a conventional process, and may be formulated alone or in combination with pharmaceutically acceptable carriers, forming agents, diluents and so on. The composition may be used in the formulation of powders, granules, tablets, capsules, injections, and the like.

Particularly, it may be employed in combination with water, phosphate buffer, extroso solution, albumin solution, antioxidants, dextrin and the like. Preferably, it may be administered intravenously or subcutaneously.

The hTPO derivatives may be administered in still less dose than native hTPO, for example, in a dosage range of about 0.01~1000 µg/kg/day.

The hTPO derivatives of this invention may be used for the treatment of thrombocytopenia caused by various conditions.

For instance, it may be useful for the treatment of thrombocytopenia caused by administration of anticancer agents, radiotherapy, bone marrow graft, hepatitis, liver cirrhosis etc. To treat these diseases, the hTPO derivatives may be administered in combination with anticancer agents such as Adriamycin and Cisplatin, and hematopoietic cytokines such as IL-3, MCSF, SCF and EPO.

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

The PCR-Amplification of cDNAs Encoding hTPO Derivatives

To induce site-specific mutagenesis in the gene encoding native hTPO, 12 pairs of oligonucleotides shown in Table 1 were prepared, which contained the specific nucleotide sequences corresponding to the mutated amino acid residues.

The established vector pBlue404 (KOREA PATENT APPLICATION NO. 97-7512) containing hTPO cDNA was employed as a template on which hTPO gene would be amplified.

In detail, PCR was carried out, employing 50 ng of pBlue404 as a template. As primers, oligonucleotide (SEQ ID NO: 1) containing the hTPO signal sequence and one of antisense oligonucleotides containing the mutated sequences (N-primers in Table 1) were used. The PCR reactions were performed in 100 µl total volume containing 4 µl of the primer solution (40 pmol/µl) and 1 µl of Pfu (; *Pyrococcus furiosus*) polymerase (2.5 u/µl; Stratagene, Cat. No. 600153). Thermocycle in the PCR was as follows: 90 sec at 94° C. for pre-denatuation; 35 amplification cycles comprising 40 sec at 94° C. for denaturation, 60 sec at 55° C. for annealing and 120 sec at 72° C. for elongation; and 5 min at 72° C. for post-elongation.

Another PCR was performed in accordance with above reaction. As PCR primers, oligonucleotide (SEQ ID NO: 2) containing hTPO C-terminal ORF and stop codon, and one of sense oligonucleotides containing the mutated sequences (C-primers in Table 1) were employed.

Obtained in the PCR were DNA fragments covering from N-terminal hTPO signal sequence to mutated sequence, and DNA fragments from the mutated sequence to hTPO C-terminal.

The PCR products were brought to 1% agarose gel electrophoresis, and then the DNA bands of interest were cut with a razor and eluted in 50 µl of tertiary distilled water with QIAEX II kit (Qiagen, Cat No. 20021).

To obtain full-length hTPO cDNAs encoding mutated hTPO, PCR in 100 µl final volume was performed, where two series of PCR products (10 ng, respectively) were employed as templates and two oligonucleotides (SEQ ID NO: 1 and NO: 2) as primers. Thermocycle in the PCR was as follows: 90 sec at 94° C. for pre-denatuation; 35 amplification cycles comprising 40 sec at 94° C. for denaturation, 60 sec at 58° C. for annealing and 120 sec at 72° C. for elongation; and 5 min at 72° C. for post-elongation.

The PCR products were brought to 1% agarose gel electrophoresis, and then the 1078-bp DNA bands were eluted in 30 µl of tertiary distilled water in accordance with said procedure.

To prepare hTPO genes containing two or more regions of mutated DNA sequences, four pairs of primers (the primers 58-N and 58-C, 60-N and 60-C, 61-N and 61-C, 63-N and 63-C) were used in PCR. The full-length cDNAs containing mutated sequence were prepared in accordance with said procedure, and then again brought to site-specific mutagenesis procedure where a primer pair 33-N and 33-C was used.

The modified amino acid and nucleotide sequences in the resulting cDNAs were shown in Table 2.

Example 2

The Construction of Mammalian Expression Vectors Containing hTPO Derivative cDNAs and Their Expression in CHO Cells (2-1) Construction of Transfer Vectors The genes encoding hTPO derivatives, which was prepared in Example 1, were subcloned in a commercially available vector pBlueBac4 (Invitrogen, Cat. No. V1995-20), as follows.

The PCR products corresponding to each hTPO derivative were digested with BglII and EcoRI enzymes at 37° C. for 3 hours, and then 1068-bp DNA fragment was isolated from the reaction mixture by 1% agarose gel electrophoresis. The 4771-bp DNA fragment was also obtained from pBlueBac4 vector digested with BglII and EcoRI enzymes.

To subclone cDNAs encoding hTPO derivatives in the pBlueBac4 vector, two DNA fragments in a molar ratio of cDNA to vector DNA fragment 4:1 were ligated by incubating them with T4 DNA ligase (NEB, Cat. No. 202S) at 16° C. for 16 hours. Then, the ligation mixtures were used to transform *E. coli* TOP10F' strain (Invitrogen, Cat. No. C3030-03) with the resulting transfer vectors. Electroporation method established already was employed to obtain the *E. coli* transformants. After these transformants were cultured in 50 ml of LB medium (10 g Trypton, 5 g Yeast extract, 10 g NaCl in one liter of water) at 37° C. for 18 hours, the transfer vectors were obtained from the cultures with Wizard Midiprep kit (Promega, Cat. No. A7640).

Figure 2:
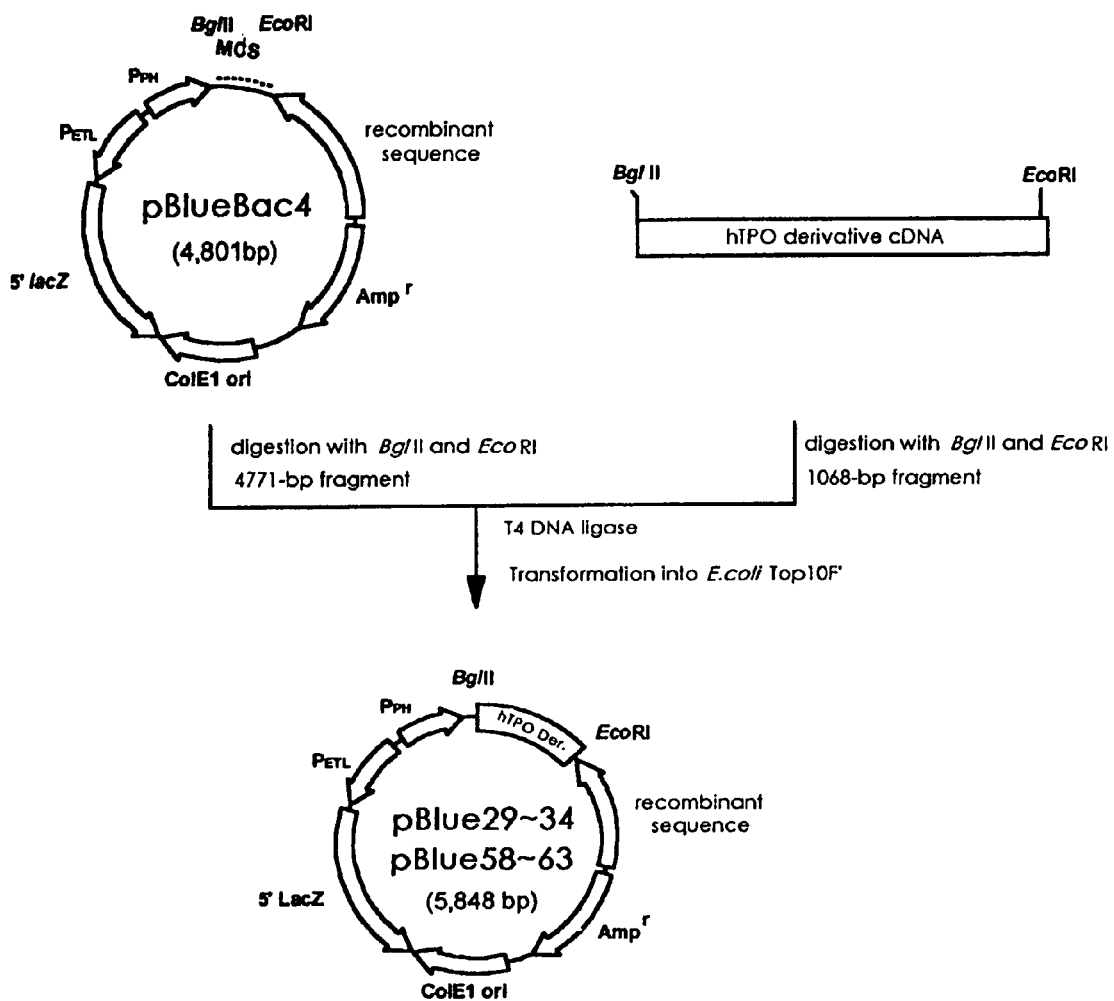
FIG. 2 depicts the process of linking the mutated genes to pBlueBac4 vector.

These transfer vectors containing hTPO derivative genes were designated pBlue29, pBlue30, pBlue31, pBlue32, pBlue33, pBlue34, pBlue58, pBlue59, pBlue60, pBlue61, pBlue62, and pBlue63, respectively (see FIG. 2)

(2—2) Construction of Animal Expression Vectors

To construct recombinant animal expression vectors containing hTPO derivative genes, pCDT was employed which was prepared by inserting wild-type hTPO gene into a commercially available vector pCDNA3.1 (Invitrogen, Cat. No. 790-20).

Particularly, 5 µg of pCDT vector was digested with EcoRI and NheI enzymes at 37° C. for 3 hours, and then 4958-bp DNA fragment was isolated from the reaction mixture by running on 1% agarose gel. The transfer vectors of Example 2-1 were digested with EcoRI and NheI enzymes, and then 1087-bp DNA fragment was also isolated from each restriction mixture.

To subclone cDNA fragments encoding various hTPO derivatives in the pCDT vector, two DNA fragments were mixed to 3:1 molar ratio and incubated with T4 DNA ligase (NEB, Cat No. 202S) at 16° C. for 18 hours. Then, the ligation mixtures were employed to transform *E. coli* TOP10F' strain (Invitrogen, Cat. No. C3030-03) with the resulting expression vectors. Electroporation method established already was employed to obtain the *E. coli* transformants (see FIG. 3). After these transformants were cultured in 50 ml of LB medium at 37° C. for 18 hours, the expression vectors were obtained from the cultures with Wizard Midiprep kit (Promega, Cat No. A7640). The animal expression vectors containing hTPO derivative genes were designated p40429, p40430, p40431, p40432, p40433, p40434, p40458, p40459, p40460, p40461, p40462, and p40463, respectively (see FIG. 3). The isolated plasmid DNA was digested with NheI, EcoRI, BamHI and Bsu36I enzymes to verify the insertion of the cDNAs. The mutation in the expression vectors was confirmed through restriction mapping and sequencing. The expression vectors were quantified by DNA electorophoresis according to Sambrook et al. (Sambrook et al., Molecular cloning—A laboratory manual, 2nd Ed., Cold spring harbor laboratory press, 1987) and used to transfect CHO/K-1 cell line.

(2-3) Expression of hTPO Derivative Genes in CHO Cells

The transfection procedure was carried out according to lipofectamin (Gibco-BRL, Cat. No. 18324012) method. On the day before transfection, CHO/K-1 cells (ATCC CCL-61) were loaded on 6-well microtiter plates at the density of $2 \times 10^5$ cells/well. After 24 hours, the cells were once washed with CHO—S—SFM II medium (Gibco-BRL, Cat. No. 12052-098) and 0.8 ml of fresh medium was added to the cells. Meanwhile, 12 µg of each expression vector was added to 600 µl of CHO—S—SFM II medium and then mixed with 600 µl of CHO—S—SFM II medium containing 36 µl of lipofectamin. After the mixture was incubated at room temperature for 30 min, 200-μl aliquots of the mixture per one well were added into the cells in 6-well plates. Then the cells were incubated at 37° C. for 5 hours in an atmosphere of 5% $CO_2$. After the addition of 1 ml of medium containing 10% FBS (Gibco-BRL, Cat. No. 16000-036) to the cells, they were further cultured at 37° C. for 24 hours in an atmosphere of 5% $CO_2$. The medium in the plates was replaced with Ham F-12 (Gibco-BRL, Cat. No. 11059) containing 10% FBS, and then the cells were further cultured at 37° C. for 72 hours in an atmosphere of 5% $CO_2$ to prepare a culture for transient expression.

In addition, after the cells in Ham F-12 medium were cultured for 48 hours, cells in one well of 6-well plates were transferred to medium containing 500 μg/ml of zeocin (Gibco-BRL, Cat. No. R25001) in 100-mm dishes. After the cells were cultured for 7~10 days, zeocin-resistant colonies were identified through microscope. Cloning cylinder (Bellco, Cat. No. 2090-01010) was used to isolate more than 12 colonies per one hTPO derivative. Gene expression levels were determined by ELISA kit for hTPO (R&D, Cat. No. DTP00), and thereby the cell lines showing the highest expression levels were selected.

Example 3

The Construction of Mammalian Expression Vectors Containing hTPO Derivative cDNAs with Two or More Modified Regions, and Their Expression in CHO Cells To produce hTPO derivatives where two or more modified amino acid regions, mammalian expression vectors of Example 2 were exploited.

In order to construct p40435, the expression vector p40429 was digested with NheI and BspMI enzymes to isolate 494-bp DNA fragment encoding a substituted amino acid ($Arg^{117}$ to $Asn^{117}$). Another expression vector p40431 was cut with BspMI and Bsu36I enzymes to isolate 355-bp DNA fragment encoding a substituted amino acid ($Gly^{147}$ to $Asn^{147}$). Additionally, animal expression vector pCDT containing hTPO cDNA was digested with NheI and Bsu36I enzymes. The fragments of p40429 and p40431 were inserted into the fragment of pCDT to construct animal expression vector p40435, which contains cDNA encoding the hTPO derivative with two modified regions ($Arg^{117}$ to $Asn^{117}$ and $Gly^{147}$ to $Asn^{147}$).

Another expression vector p40436 is associated with two amino acid substitutions ($Arg^{117}$ to $Asn^{117}$ and $Arg^{164}$ to $Asn^{164}$) and was prepared by inserting the 494-bp fragment of p40429 and 593-bp BspMI-EcoRI fragment of p40433 into pCDT.

Expression vectors such as p40437, p40438, and p40439, were prepared in accordance with the above procedure, where two DNA fragments encoding substituted amino acids were isolated from the corresponding vector and inserted into the expression vector pCDT (see Table 3).

Other expression vectors such as p40446, p40447, or p40449, were prepared according to a procedure where three DNA fragments encoding substituted amino acids were isolated from the corresponding vector and inserted into pCDT (see Table 3).

These eight vectors obtained here were transfected into CHO/K-1 cells in 6-well plates. According to the procedure of Example 2, cultures for transient expression were prepared, and zeocin-resistant colonies were isolated, respectively.

Example 4

Estimation of In Vitro Activities of hTPO Derivatives: M-07e Cell Proliferation Assay To prepare hTPO derivatives, the transfected cell lines of Example 2 and 3 were cultured in Cell Factory (Nunc, Cat. No. 170009) on 10-liter scale. Each transfected cells ($5 \times 10^4$ cells/ml) were transferred into Cell Factory containing Ham F-12 medium supplemented with 10% FBS. Cultured for 72 hours, the cells were washed once with PBS and then cultured in ExCell medium (JRH, Cat. No. 14311-10L). After the cells were further cultured at 37° C. for 96 hours in an atmosphere of 5% $CO_2$, supernatants were obtained from the culture. The supernatants were concentrated first with pelicon membrane (Millipore, Cat. No. 42PEL60) and second with minitan membrane (Millipore, Cat. No. 80EL004). After concentration, each sample was brought to dialysis in 1×TNT buffer (10 mM Tris, 0.15 M NaCl, 0.01% Tween 20, pH 7.4) at 4° C. for 30 hours, followed by third concentration with Ultrafree (Millipore, Cat. No. UFV2BGC10). The samples were quantified with ELISA kit three times.

Megakaryocyte leukemia cell line M-07e was maintained in RPMI1640 medium (Gibco-BRL, Cat. No. 22400-089) supplemented with GM-CSF (100 u/ml) and 10% FBS.

To estimate activity, assay medium (RPM1640 supplemented with 5% FBS) was prepared, and M-07e cells were harvested by centrifugation, then washed with RPM1640 three times. The cells were resuspended in the assay medium, adjusted to $8 \times 10^4$ cells/ml in T-75 flask, and cultured for 24 hours in an atmosphere of 5% $CO_2$. Again, the cells were harvested and adjusted to $1 \times 10^5$ cells/ml. 100 μl aliquots of the cell suspension were added to 96-well plates. Eight-step concentrations (100.0~0.78125 ng/ml) of standard material (rhTPO, 25 μg) were prepared by serial dilution with RPMI1640 medium, and CHO cell-derived native hTPO was employed as control. Total 11 species of hTPO derivatives (from 40429 to 40439) were prepared at the concentration of 1.5625, 6.25 and 25 ng/ml. A 100-μl aliquot of each sample per well was added, adjusting to 200 μl/well. After incubated for 20 hours in an atmosphere of 5% $CO_2$, the cells were fed with 1 μCi (37 kBq) of $^3$H-Thymidine and further incubated for 4 hours. Then, cells were harvested using cell harvester equipped with a glass fiber filter, which was washed with PBS seven times.

The filters in which cells were harvested were put in counting vials one by one, and $^3$H-radioactivities emitted from each sample were measured with a liquid scitilation counter. Riasmart software was used to calculate the half-maximal concentration of standards, contol and samples.

All derivatives showed similar patterns of activities stimulating M-07e cell proliferation. At the concentration of 25 ng/ml, 8 species of derivatives 40429, 40430, 40432, 40433, 40434, 40437, 40438 and 40439 showed similar or higher activities than native hTPO did, their activities amounting to 117, 135, 120, 131, 97, 121, 166 and 133% of native hTPO activity (see FIG. 4).

Example 5

In Vivo Activities of hTPO Derivatives Isolated from CHO Cells

Figure 6:
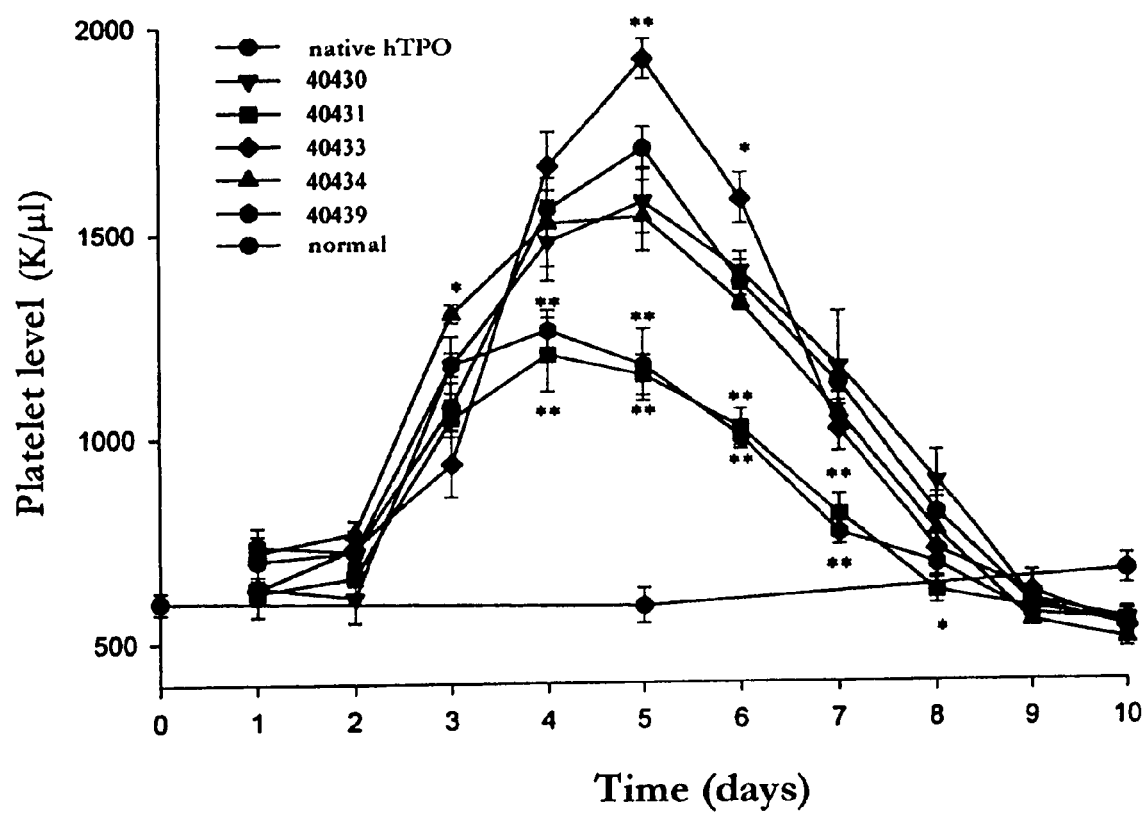
FIG. 6. presents the in vivo activities of various hTPO derivatives, which are determined by measuring the number of platelets in mouse blood after treatment with hTPO derivatives (36 μg/kg) expressed in animal cells.
Figure 7A:
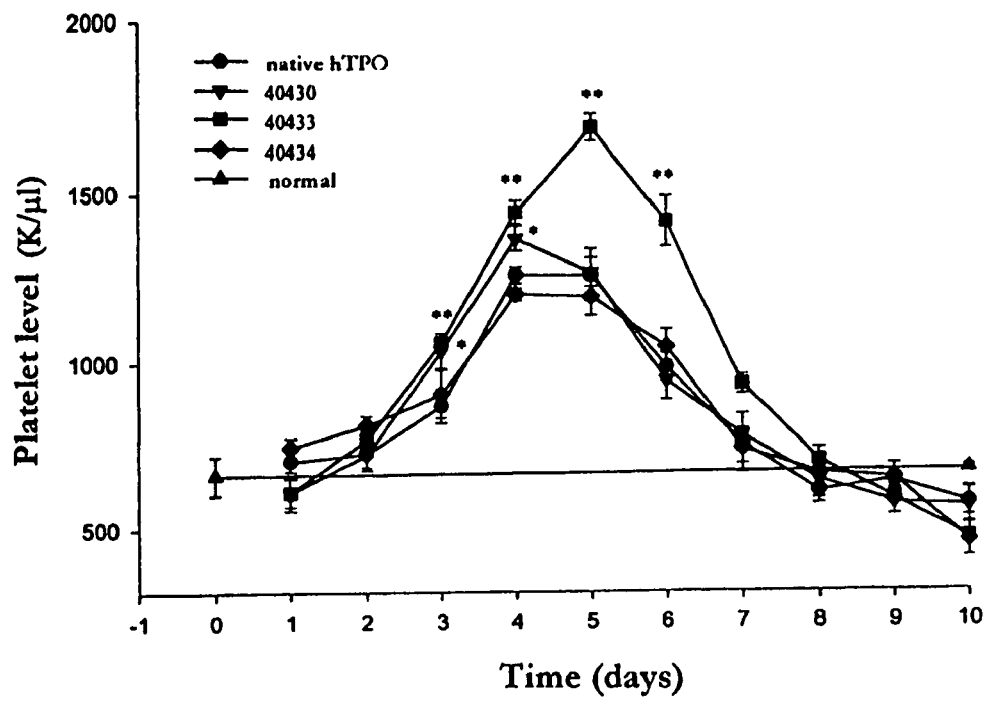
FIGS. 7a and 7b present the in vivo activities of various hTPO derivatives, which are determined by measuring the number of platelets in mouse blood after treatment with hTPO derivatives (10 μg/kg) expressed in animal cells.
Figure 7B:
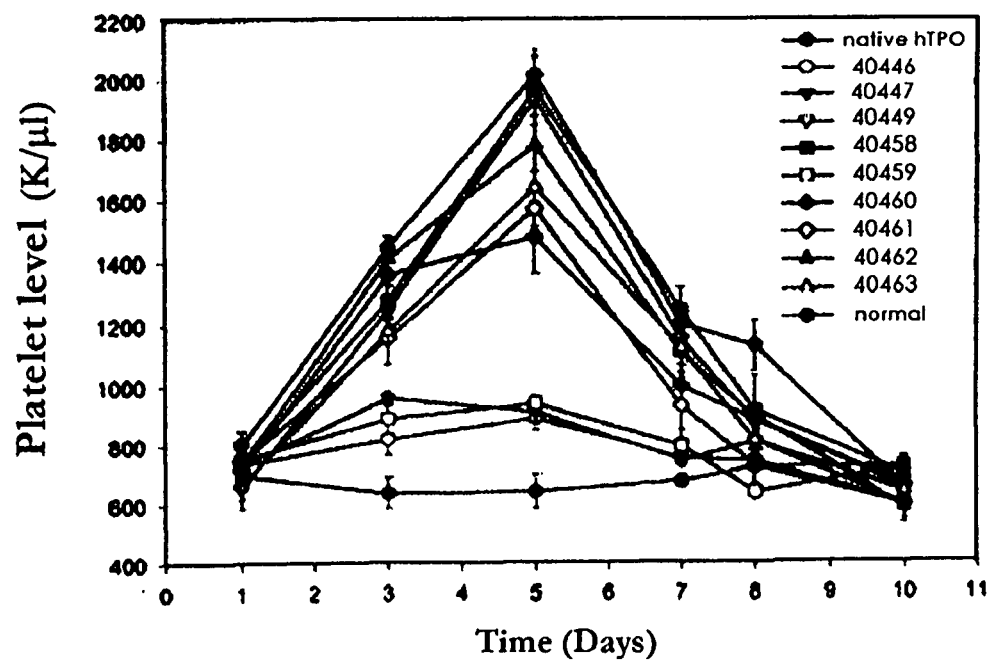

In vivo hTPO assay was carried out where platelet levels were determined in the mice treated with various hTPO derivatives of this invention, and FIGS. 6, 7a and 7b give the results. 7-week female Balb/c mice (Charles River, Japan) were adapted in a conditioning room (24±1° C., 55% R.H., lighting for 12 hours, from 7:00 a.m. to 7:00 p.m.) for a week. The 8-week mice were brought to the assay and kept in the domestication room during the test.

The mice were randomly divided into groups comprising 5 mice on the basis of weights. The groups were specified as groups treated with medium only, treated with native hTPO, treated with each hTPO derivative of this invention, or not treated, respectively.

Various hTPO derivatives (36 µg/kg or 10 µg/kg) were subcutaneously administered to the mice in single injection, and the blood samples of mice were collected everyday from day 0 (the day of injection) to day 10. Samples were collected from abdominal vena cava within 24 hours after administration. Whole blood in EDTA-treated tube was set on automatic hemocytometer (Cell dyn 3500, Abbott), by which platelet levels in samples were measured. The results were presented in 'mean±standard error'.

On day 3, native hTPO stimulated an increase in platelet level. The platelet level reached a maximum on day 5 and came to normal level on day 10. All derivatives were found to stimulate an increase in platelet level, and derivatives 40433, 40434, 40449 and 40458 produced equal or higher platelet levels than native hTPO did. Especially, 40433 showed approximately 34% higher maximal in vivo activity of platelet production on day 5 than native hTPO, and 80% or more in total.

Comparative Example 1

In Vivo Activity of Native hTPO

Figure 5:
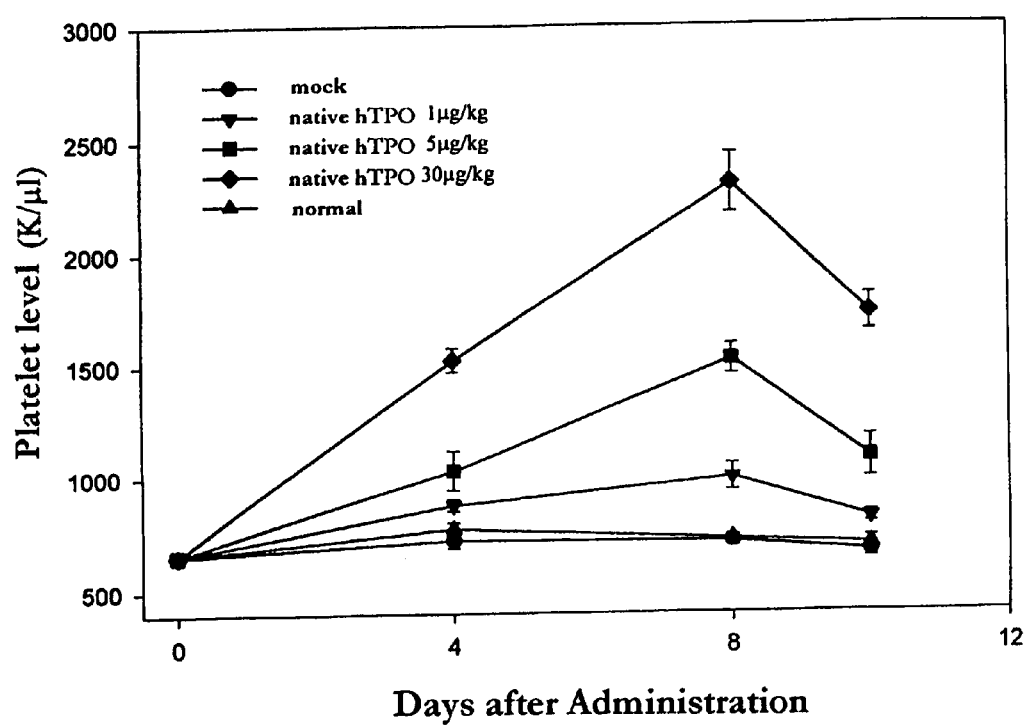
FIG. 5 presents the in vivo activity of native hTPO, which is determined by measuring the number of platelets in mouse blood after treatment with various doses of native hTPO.

FIG. 5 shows the platelet level in a mouse that was treated with native hTPO derived from animal cells. 7-week female Balb/c mice (Charles River, Japan) were adapted in a conditioning room (24±1° C., 55% R.H., lighting for 12 hours, from 7:00 a.m. to 7:00 p.m.) for a week. The 8-week mice were brought to the assay and kept in the domestication room during the test.

The mice were randomly divided into groups comprising 5 mice on the basis of weights. The groups were specified as groups treated with medium only, treated with native hTPO, or not treated, respectively. Various concentrations (1, 5 and 10 µg/kg) of native hTPO were subcutaneously administered in single injection, and the blood samples of mice were harvested on day 4, 8 and 10 (where day 1 is the day of injection). Sample was harvested from abdominal vena cava within 24 hours after administration. Whole blood in EDTA-treated tube was set on automatic hemocytometer (Cell dyn 3500, Abbott), by which platelet levels in samples were measured. The results were presented in 'mean±standard error'. Native hTPO stimulated an increase in platelet level from day 4. The platelet level reached a maximum on day 8 and came down to 80% of the maximal value on day 10.

Example 6

Construction of dhfr Expression Vectors Containing hTPO Derivative cDNAs, and Selection of Mammalian Cell Lines Expressing Them (6-1) Construction of dhfr Expression Vectors Containing hTPO Derivative cDNAs According to the result of Example 5, dhfr expression vectors were constructed, which corresponding to the derivatives 40433, 40434, 40449 and 40458.

At first, BamHI linker was inserted into pSV-dhfr (ATCC 37146) containing dhfr gene. To prepare BamHI linker, two oligonucleotides (SEQ ID NO: 27 and NO: 28) were phosphorylated and then annealed to hybridize with each other. Particularly, T4 polynucleotide kinase (NEB, Cat. No. 201S) was used in the phosphorylation reaction at 37° C. for 3 hours. In the annealing reaction, the equimolar oligonucleotides were mixed and placed at 94° C. for 2 min, then the mixture was stepwisely cooled down from 65° C. to 37° C. with the temperature decreased by 0.2° C. per 30 sec. The vector pSV2-dhfr was restricted with PvuII and SphI enzymes, then the BamHI linker was connected with the fragment of pSV2-dhfr. The resulting vector was digested with BamHI enzyme in order to prepare the 1710-bp fragment containing dhfr gene.

After the expression vector pCDT containing wild-type hTPO gene was digested with BglII enzyme, the 1710-bp fragment were inserted into the pCDT. The resulting dhfr expression vector expressing native hTPO was designated pDCT (see FIG. 8).

To dhfr expression vectors corresponding to 5 derivatives, two oligonucleotides (SEQ ID NO: 29 and NO: 2) were employed as PCR primers. Except for primers, the PCR was performed under the same condition as in Example 1. Amplified DNA sequences encoding hTPO derivatives were cut with KpnI and EcoRI enzymes, and then inserted into the KpnI-EcoRI site of the pDCT vector. The resulting vectors were designated pD40433, pD40434, pD40449 and pD40458, respectively.

(6-2) Transfection Into CHO/dhfr(-) Cell Line and Gene Amplification

The dhfr expression vectors of Example 6-1 were transfected into animal cell line CHO/dhfr(-) (ATCC CRL-9096) according to the transfection procedure of Example 2. IMDM medium (Gibco-BRL, Cat. No. 12200-036) was used for the transfection, and IMDM medium supplemented with 10% dialyzed FBS (Gibco-BRL, Cat. No. 26300-061) for subsequent culture.

To select transformed line, the cells were added to 96-well microtiter plates ($1\times10^3$ cells/well) in 48 hours after transfection, and cultured for 10-14 days in medium containing 500 µg/ml zeocin. Zeocin-resistant colonies were isolated, and the 10-20 cell lines producing higher expression levels were selected by ELISA quantification.

The selected cell lines were subcultured in medium containing 20 nM MTX (Methotrexate, Sigma, Cat. No. M8407) to amplify hTPO gene. In detail, the cells were cultured in T-25 flask until flask was saturated with the cells. One-fifth of the saturated cells were subcultured, then 1/10 and 1/15, successively. Amplification finished when T-25 flask was saturated with cells in 3-4 days after the 1/15 subculture. Cell lines producing highest expression levels were selected by ELISA from amplified cell lines in 20 nM MTX. The cell lines were used to prepare samples for in vivo hTPO assay.

Example 7

Expression of Native hTPO and Derivatives Thereof in CHO/dhfr(-) Cells, and Their Purification To prepare native hTPO and derivatives thereof, the cell lines of Example 6 were cultured in Cell Factory (Nunc, Cat.

No. 170069) on 4-liter scale. Each cell line ($5 \times 10^4$ cells/ml) was transferred into Cell Factory containing IMDM medium supplemented with 10% FBS. Cultured for 72 hours, the cells were washed once with PBS and then cultured in DMEM/Ham F-12 medium. After the cells were further cultured at 37° C. for 96 hours in an atmosphere of 5% $CO_2$, supernatants obtained from the culture were brought to purification steps.

After XK26/20 column (Amersham-pharmacia, Cat. No. 18-1000-72) was filled with 50 ml of CM Affi-Gel blue resin (Bio-Rad, Cat. No. 153-7304), the column was washed with buffer A (10 mM sodium phosphate, 150 mM sodium chloride, pH 7.4) overnight. 4-liter of the culture supernatants was loaded and passed through the column with the flow rate of 5 ml/min, and was monitored by spectrophotometry at UV wavelength 280 nm. After the whole culture supernatant was distributed throughout the column, the column was washed with buffer B (10 mM sodium phosphate, 2 M urea, pH 7.4) until the UV absorption dropped to basal level. Bound proteins including hTPO were eluted with buffer C (10 mM sodium phosphate, 2 M urea, 1 M sodium chloride, pH 7.4), and this fraction was applied to subsequent phenylsepharose column chromatography. XK26/20 column was filled with 50 ml of phenylsepharose CL4B resin (Sigma, Cat. No. P7892) and then washed with buffer C overnight. The fraction eluted from CM Affi-Gel blue column was applied to the pheylsepharose column with flow rate of 3 ml/min and monitored by spectrophotometry at UV wavelength 280 nm. After the whole culture supernatant was distributed throughout the column, the column was washed with buffer C until the UV absorption dropped to basal level. Proteins bound to resin were eluted with buffer B and this fraction was applied to subsequent hydroxylapatite column chromatography. XK16/20 column (Amersham-pharmacia, Cat. No. 18-8773-01) was filled with 10 ml of hydroxylapatite resin (Bio-Rad, Cat. No. 130-0420) and washed with buffer D (10 mM sodium phosphate, 2 M urea, pH 6.8) overnight. The fraction eluted from the pheylsepharose column was adjusted to pH 6.8 with 5 N HCl and then applied to hydroxylapatite column with flow rate of 3 ml/min. Since hTPO is not bound to hyroxylapatite resin, the unbound fraction was reserved. The column was washed with buffer D until the UV absorption dropped to basal level. Then, impure proteins bound to resin were eluted with buffer E (0.5 M sodium phosphate, 2 M urea, pH 6.8). The obtained hTPO fraction was concentrated to 10-ml volume using Econo-Pac Q cartridge (Bio-Rad, Cat. No. 732-0021), and then dialyzed in 10 mM sodium phosphate for 24 hours to eliminate salts and urea. Each fraction in the purification steps was visualized through SDS-PAGE and silver staining (see FIG. 9), where Silver-stain Plus kit (Bio-Rad, Cat. No. 161-0449) was used in accordance with the manufacturer's instruction.

In vivo hTPO assay was performed with the purified hTPO derivatives (dose: 10 μg/kg) according to the method of Example 5. All derivatives were found not only to stimulate an increase in platelet level, but also to produce higher platelet levels than native hTPO did. Particularly, 40433, 40434, 40449, and 40458 showed 77%, 91%, 26%, and 79% higher activities for total 10 days after administration than native hTPO, respectively (see FIG. 10).

Example 8

Characterization of hTPO Derivatives: Verifying the Introduction of Sugar Chains and Examining the Stability of hTPO Derivatives To investigate whether additional sugar chains were introduced into the hTPO derivatives, SDS-PAGE and Western blot analysis was performed. If sugar chains are introduced, the molecular weights of hTPO derivatives will be heavier than that of native hTPO.

Figure 11:
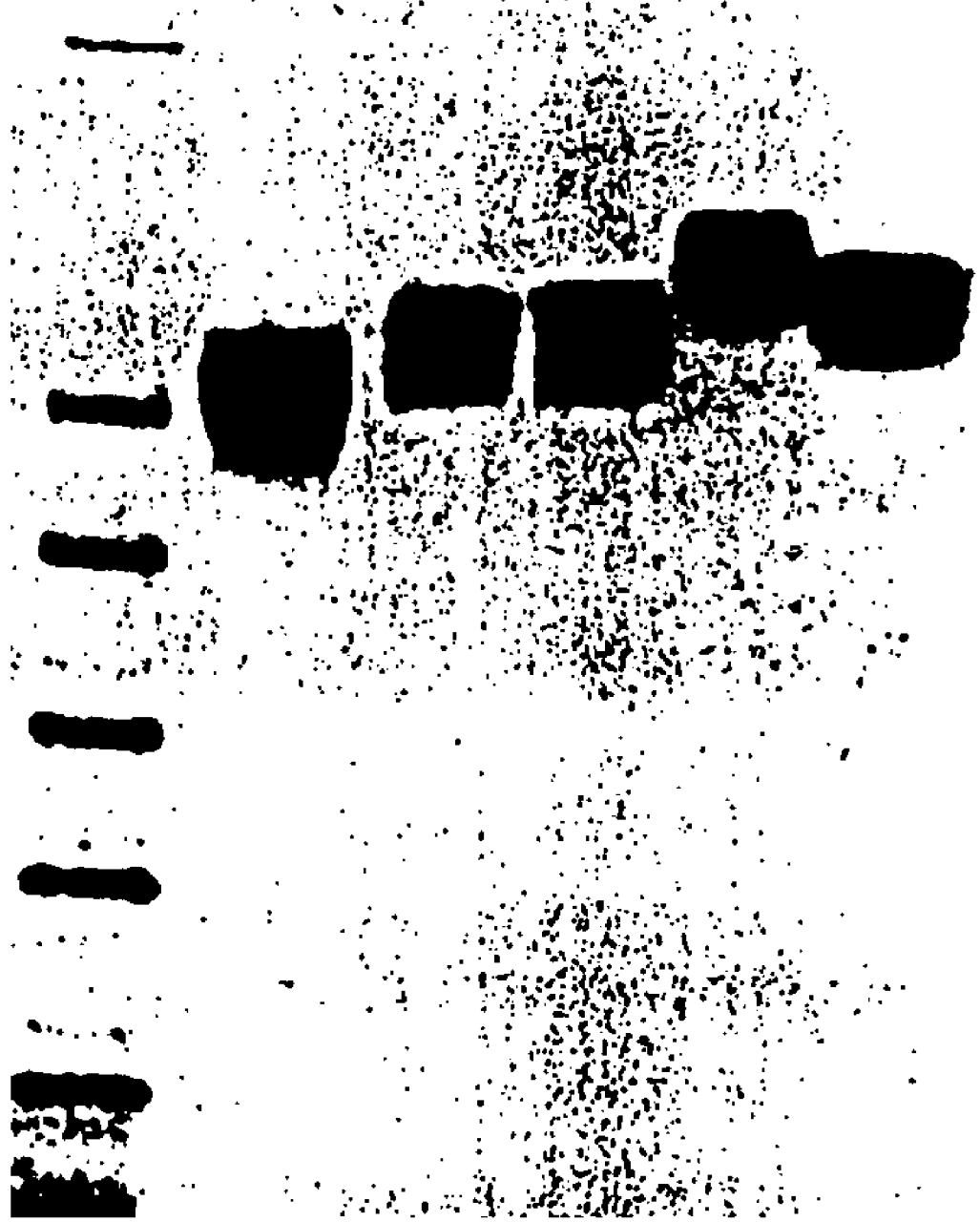
FIG. 11 presents the result of SDS-PAGE and western blot analysis with the purified native hTPO and hTPO derivatives, where
lane M: size marker;
lane 1: native hTPO;
lane 2: hTPO derivative 40433;
lane 3: hTPO derivative 40434;
lane 4: hTPO derivative 40449;
lane 5: hTPO derivative 40458.

Purified native hTPO and derivatives thereof were loaded into wells in 10~20% gradient tricine polyacrylamide gel (Novex, Cat. No. EC66252), which was run at a voltage of 10 V/cm. After electrophoresis, the proteins fractionated on the gel were transferred onto a nitrocellulose filter. The filter was incubated for 1 hour in TBS (pH 7.5) containing 5% non-fat dried milk, and then further incubated for 18 hours with goat anti-hTPO polyclonal antibody (R&D system, Cat. No. AB-288-NA) diluted in TBS (1:1000). The filter was subsequently incubated for 2 hours with a seconday antibody, alkaline phosphatase-conjugated anti-goat IgG (Sigma, Cat. No. A4187) diluted in TBS (1:10000). The coloring substrate BCIP/NBT (Sigma, Cat. No. B5655) was used for detecting hTPO band. In result, molecular weights of purified hTPO derivatives were heavier than that of native hTPO, depending on the number of sugar chains introduced (FIG. 11).

To evaluate the stability of hTPO derivatives, native hTPO and a hTPO derivative 40433 were digested with Thrombin, and then the time-dependent digestion patterns were observed. The hTPO derivative (50 μg/ml) was treated with Thrombin (5 units/ml, Sigma, Cat. No. T6759) at 37° C. for 0.5, 1, 2, 3, 4, or 6 hours. Then, SDS-PAGE and Western blot analysis was performed to observe the digestion patterns. Native hTPO was strikingly degraded in 30 min after treatment with Thrombin, while the derivative 40433 was digested in 4 hours (see FIG. 12). This result verified that the derivative 40433 is more stable than native hTPO, which can be explained from the sugar chain introduced.

INDUSTRIAL APPLICABILITY

As shown above, the hTPO derivatives of this invention induce the production of platelet precursor cells in vivo, and thus are useful for the treatment of thrombocytopenia associated with anticancer therapies or bone marrow graft. Especially, the hTPO derivatives 40433, 40434, 40449 and 40458 show significantly higher efficacy inducing platelet production than native hTPO, providing various advantages. Since low dose of hTPO derivatives shows similar efficacy to native hTPO, small dose of hTPO can be infrequently administered to the patients suffering from thrombocytopenia. Therefore, use of derviatives of this invention will reduce the cost of treating the disease and will elevate the welfare of patients as well as the safety of the drug, with the inclusion of impure proteins excluded, owing to the small dose used.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A human thrombopoietin derivative which is derived from human thrombopoietin (hTPO) described by SEQ ID NO: 30; by the introduction at least one additional N-linked glycosylation site; and which comprises substitutions of Asn for Pro and Arg, respectively, at residues 157 and 164 relative to SEQ ID NO: 30.

2. A recombinant gene encoding a human thrombopoietin derivative of claim 1.

3. A eukaryotic expression vector containing the recombinant gene of claim 2.

4. The eukaryotic expression vector of claim 3 which is p40458.

5. A mammalian cell line CHO dhfr-/pD40458 (Accession NO: KCTC 0632BP) transfected with the expression vector pD0458 of claim 4.

6. A process of preparing a human thrombopoietin derivative comprising culturing a mammalian cell line containing the recombinant gene of claim 2 and obtaining a human thrombopoietin derivative from the cultured mammalian cell line.

7. A pharmaceutical composition containing the human thrombopoietin derivative of claim 1.

* * * * *